United States Patent
Matsui et al.

(10) Patent No.: US 10,472,617 B2
(45) Date of Patent: *Nov. 12, 2019

(54) THERMOSTABLE ASPARAGINASE VARIANTS AND POLYNUCLEOTIDES ENCODING SAME

(71) Applicant: Novozymes A/S, Bagsvaerd (DK)

(72) Inventors: Tomoko Matsui, Chiba (JP); Aki Tomiki, Chiba (JP); Allan Svendsen, Hoersholm (DK); Hanne Vang Hendriksen, Holte (DK); Mary Ann Stringer, Soeborg (DK); Keiichi Ayabe, Chiba (JP)

(73) Assignee: Novozymes A/S, Bagsvaerd (DK)

( * ) Notice: Subject to any disclaimer, the term of this patent is extended or adjusted under 35 U.S.C. 154(b) by 113 days.

This patent is subject to a terminal disclaimer.

(21) Appl. No.: 15/714,292

(22) Filed: Sep. 25, 2017

(65) Prior Publication Data

US 2018/0030428 A1    Feb. 1, 2018

Related U.S. Application Data

(62) Division of application No. 14/420,399, filed as application No. PCT/EP2013/067079 on Aug. 15, 2013.

(60) Provisional application No. 61/684,999, filed on Aug. 20, 2012.

(30) Foreign Application Priority Data

Aug. 17, 2012  (EP) .................................... 12180861

(51) Int. Cl.
  *C12N 9/82* (2006.01)
  *A23L 5/20* (2016.01)

(52) U.S. Cl.
  CPC .................. *C12N 9/82* (2013.01); *A23L 5/25* (2016.08); *C12Y 305/01001* (2013.01)

(58) Field of Classification Search
  CPC .... C12Y 305/01001; A23L 5/25; A23L 29/06; C12N 9/82
  See application file for complete search history.

(56) References Cited

U.S. PATENT DOCUMENTS

| | | | |
|---|---|---|---|
| 7,396,670 B2 | 7/2008 | Budolfsen |
| 7,666,652 B2 | 2/2010 | Matsui |
| 7,829,320 B2 | 11/2010 | Matsui |
| 8,124,396 B2 | 2/2012 | Budolfsen |
| 8,323,948 B2 | 12/2012 | Van der Laan |
| 8,507,246 B2 | 8/2013 | Budolfsen |
| 8,859,023 B2 | 10/2014 | Budolfsen |
| 9,057,087 B2 | 6/2015 | Prata |
| 2005/0064084 A1 | 3/2005 | Elder |
| 2006/0275879 A1 | 12/2006 | Lynglev |
| 2007/0141227 A1 | 6/2007 | Boudreaux |
| 2008/0096260 A1 | 4/2008 | Budolfsen |
| 2009/0170157 A1 | 7/2009 | Matsui |
| 2010/0136169 A1 | 6/2010 | Van der Laan |
| 2011/0052758 A1 | 3/2011 | Greiner-Stoeffele |
| 2011/0256267 A1 | 10/2011 | Hendriksen |
| 2012/0045549 A1 | 2/2012 | Van der Laan |
| 2013/0330785 A1 | 12/2013 | Prata |
| 2014/0314908 A1 | 10/2014 | Hendriksen |
| 2015/0210995 A1 | 7/2015 | Matsui |
| 2015/0240265 A1 | 8/2015 | Prata |
| 2015/0320089 A1 | 11/2015 | Hendriksen |
| 2015/0359246 A1 | 12/2015 | Hendriksen |
| 2016/0037807 A1 | 2/2016 | Hendriksen |

FOREIGN PATENT DOCUMENTS

| | | |
|---|---|---|
| WO | 2004/026042 A1 | 4/2004 |
| WO | 2004/032648 A1 | 4/2004 |
| WO | 2007/077546 A1 | 7/2007 |
| WO | 2008/110513 A1 | 9/2008 |
| WO | 2008/128974 A1 | 10/2008 |
| WO | 2008/128975 A1 | 10/2008 |
| WO | 2010/070010 A2 | 6/2010 |
| WO | 2011/134916 A1 | 11/2011 |

OTHER PUBLICATIONS

Fedorova et al., UniProt Accession No. B0XML5 (2008).
Galagan et al., UniProt Accession No. Q5BGN0 (2005).
Hendriksen et al., J. Agric. Food Chem., vol. 57, No. 10, pp. 4168-4176 (2009).
Hendriksen et al., Alignment of Sequence 1 of U.S. Appl. No. 13/132,005 and sequence in U.S. 2011/0256267 (2011).
Pedreshi et al., Food Chemistry, vol. 109, No. 2, pp. 386-392 (2007).

*Primary Examiner* — Kagnew H Gebreyesus
(74) *Attorney, Agent, or Firm* — Elias Lambiris

(57) ABSTRACT

The present invention relates to asparaginase variants. The present invention also relates to polynucleotides encoding the variants; nucleic acid constructs, vectors, and host cells comprising the polynucleotides; and methods of using the variants. The invention further relates to a process of producing a fermentation product, comprising: liquefying a starch-containing material to dextrins with an alpha-amylase in the presence of an asparaginase of the invention; saccharifying the dextrins to a sugar with a glucoamylase; and fermenting the sugar using a fermenting organism.

19 Claims, 1 Drawing Sheet
Specification includes a Sequence Listing.

$$\text{STARCH} + \text{IODINE} \xrightarrow[40°, \text{pH } 2{,}5]{\text{ALPHA - AMYLASE}} \text{DEXTRINS} + \text{OLIGOSACCHARIDES}$$

$\lambda = 590$ nm blue/violet          t = 23 sec.     decoloration

THERMOSTABLE ASPARAGINASE VARIANTS AND POLYNUCLEOTIDES ENCODING SAME

CROSS-REFERENCE TO RELATED APPLICATIONS

This application is a division of U.S. application Ser. No. 14/420,399 filed Feb. 9, 2015, now U.S. Pat. No. 9,828,595, which is a 35 U.S.C. 371 national application of international application no. PCT/EP2013/067079 filed Aug. 15, 2013, which claims priority or the benefit under 35 U.S.C. 119 of European application no. 12180861.2 filed Aug. 17, 2012 and U.S. provisional application No. 61/684,999 filed Aug. 20, 2012. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to asparaginase variants, polynucleotides encoding the variants, methods of producing the variants, and methods of using the variants. The present invention further relates to processes of producing sugars, dextrins and fermentation products from plant material using one or more fermenting organisms.

Description of the Related Art

It is well known that acrylamide formation in heated food products may be reduced by a treatment reducing the amount of asparagine in the food materials, such as by subjecting the food materials to the action of the enzyme asparaginase (see, e.g., WO 2004/026042).

A number of fungal asparaginases have been identified; see, e.g., WO 2004/030468 or WO 2004/032648. Protein engineering of such asparaginases to improve their properties has been described. WO 2008/128974, WO 2008/128975 and WO 2011/134916 disclose variants of asparaginase from A. niger having an improved activity at more alkaline pH. WO 2008/110513 discloses variants of asparaginase from A. oryzae having an improved thermostability. However, in certain industrial applications of asparaginase, e.g., in the production of French fries, an even higher thermostability is desired.

It is an object of the present invention to provide asparaginase variants with improved properties compared to its parent.

A vast number of commercial products that are difficult to produce synthetically are today produced by fermenting organisms. Such products include alcohols (e.g., butanol, ethanol, methanol, 1,3-propanediol); organic acids (e.g., acetic acid, citric acid, gluconate, gluconic acid, itaconic acid, lactic acid, succinic acid, 2,5-diketo-D-gluconic acid); ketones (e.g., acetone); amino acids (e.g., glutamic acid); gases (e.g., H2 and CO2), and more complex compounds, including, for example, antibiotics (e.g., penicillin and tetracycline); enzymes; vitamins (e.g., riboflavin, B12, beta-carotene); and hormones. Fermentation is also commonly used in the consumable alcohol (e.g., beer and wine), dairy (e.g., in the production of yogurt and cheese), leather, and tobacco industries.

A vast number of processes of producing fermentation products, such as ethanol, by fermentation of sugars provided by degradation of starch-containing materials are known in the art.

However, production of, sugars, dextrins and fermentation products, such as ethanol, from such plant materials is still too costly. Therefore, there is a need for providing processes that can increase the yield of the fermentation product and thereby reduce the production costs.

It is a further object of the present invention to provide an improved process for producing a fermentation product.

SUMMARY OF THE INVENTION

In one aspect, the present invention relates to an asparaginase variant comprising a substitution at one or more positions corresponding to positions 140 or 241 of SEQ ID NO: 2, or a deletion at a position corresponding to position 27 of SEQ ID NO: 2, wherein the variant has at least 50% sequence identity to the mature polypeptide of any of SEQ ID NO: 2 or 4, and wherein the variant has asparaginase activity.

In another aspect, the present invention relates to an asparaginase variant comprising a substitution at one or more positions corresponding to positions 122, 140, 197, 238, 239, 240, 241, 253, 258, 259, 297 or 373 of SEQ ID NO: 2, or a deletion at one or more positions corresponding to position 27, 28 or 29 of SEQ ID NO: 2, wherein the variant has at least 80% sequence identity to the mature polypeptide of any of SEQ ID NO: 2 or 4, and wherein the variant has asparaginase activity.

In another aspect, the present invention relates to an asparaginase variant comprising (i) one or more of the following substitutions, wherein each position corresponds to a position in SEQ ID NO: 2: T71C, T74C, K122A, V139G, T140D, K194L, D197E, S238C, N239C, K240R, P241E, K253R, I258Y, R259C, R259V, S334W, S338W, G356D, K363R or E373H, or (ii) a deletion at a position corresponding to position 27 of SEQ ID NO: 2; wherein the variant has at least 50% sequence identity to the mature polypeptide of any of SEQ ID NO: 2 or 4, and wherein the variant has asparaginase activity.

In another aspect, the present invention relates to an asparaginase variant comprising (i) one or more of the following substitutions, wherein each position corresponds to a position in SEQ ID NO: 2: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H, or (ii) a deletion at one or more positions corresponding to positions 27, 28 or 29 of SEQ ID NO: 2; wherein the variant has at least 80% sequence identity to the mature polypeptide of any of SEQ ID NO: 2 or 4, and wherein the variant has asparaginase activity.

In another aspect, the present invention relates to an asparaginase variant having a melting temperature Tm of at least 76° C., preferably at least 77° C., at least 78° C., at least 79° C. or at least 80° C., e.g., at least 81° C., at least 82° C., at least 83° C., at least 84° C. or at least 85° C., where the Tm is determined by Differential Scanning calorimetry, and having at least 50% sequence identity to the mature polypeptide of any of SEQ ID NO: 2 or 4.

The present invention also relates to isolated polynucleotides encoding the variants; nucleic acid constructs, vectors, and host cells comprising the polynucleotides; and methods of producing the variants.

The present invention also relates to methods of using the variants in the production of a food product.

The present invention also relates to methods of obtaining the variants.

The present invention also relates to a process of producing a fermentation product, comprising:
(a) liquefying a starch-containing material to a dextrin with an alpha-amylase in the presence of an asparaginase of the invention;
(b) saccharifying the dextrin to a sugar with a saccharifying enzyme; and
(c) fermenting the sugar using a fermenting organism to produce the fermentation product.

The present invention also relates to a process of producing a sugar, comprising:
(a) liquefying a starch-containing material to a dextrin with an alpha-amylase in the presence of an asparaginase of the invention; and
(b) saccharifying the dextrin to a sugar with a saccharifying enzyme.

The present invention also relates to a process of producing a fermentation product, comprising:
(a) treating a starch-containing material with an asparaginase of the invention;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.

The present invention also relates to a process of producing a dextrin, comprising
(a) liquefying a starch-containing material to the dextrin with an alpha-amylase in the presence of an asparaginase of the invention; and
(b) recovering the dextrin.

The present invention also relates to a process of producing a fermentation product, comprising:
(a) treating a starch-containing material with an asparaginase of the invention;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.

The present invention also relates to a process of producing a sugar, comprising:
(a) treating a starch-containing material with an asparaginase of the invention;
(b) liquefying the treated starch-containing material to a dextrin with an alpha-amylase; and
(c) saccharifying the dextrin to a sugar with a saccharifying enzyme.

The present invention also relates to a process of producing a dextrin, comprising:
(a) treating a starch-containing material with an asparaginase of the invention; and
(b) liquefying the treated starch-containing material to a dextrin with an alpha-amylase.

The present invention also relates to a process of producing a fermentation product, comprising converting a starch-containing material to a dextrin with an alpha-amylase; saccharifying the dextrin to a sugar with a glucoamylase; and fermenting the sugar using a fermenting organism in the presence of an asparaginase of the invention in a single step at a temperature below the initial gelatinization temperature of the starch-containing material.

The present invention also relates to a process of producing a fermentation product, comprising
(a) treating a plant extract containing amino acid(s) and soluble sugar(s) with an asparaginase of the invention;
(b) producing molasses from the plant extract;
(c) diluting the molasses; and
(d) fermenting the diluted molasses with a fermenting organism to produce ethanol.

The present invention also relates to a process of producing a fermentation product, comprising
(a) treating a plant extract containing amino acid(s) and soluble sugar(s) with an asparaginase of the invention; and
(b) fermenting the treated plant extract with a fermenting organism to produce the fermentation product.

The present invention also relates to a process of producing a sugar, comprising
(a) treating a plant extract containing amino acid(s) and soluble sugar(s) with an asparaginase of the invention; and
(b) recovering the sugar from the treated plant extract.

The present invention also relates to a process of producing sucrose, comprising:
(a) treating a plant extract containing amino acid(s) and soluble sugar(s) with an asparaginase of the invention;
(b) clarification of the plant extract;
(c) concentration of sugars found in the clarified plant extract (e.g., by evaporation) to form a syrup containing sucrose;
(d) crystallization of sucrose from the syrup; and
(e) recovering sucrose.

BRIEF DESCRIPTION OF THE DRAWINGS

The FIGURE depicts the chemical reaction of the reduction in the concentration of starch under the specified analytical conditions for determining acid alpha-amylase activity (AFAU).

Definitions

Alpha-amylases (alpha 1,4-glucan 4 glucanohydrolases, EC 3.2.1.1) are a group of enzymes, which catalyze the hydrolysis of starch and other linear and branched 1,4 glucosidic oligo and polysaccharides.

Asparaginase: The term "asparaginase" means an enzyme having asparaginase activity, i.e., an enzyme that catalyzes the hydrolysis of asparagine to aspartic acid (EC 3.5.1.1). Asparaginase activity may be determined according to one of the asparaginase activity assays described in the Examples, e.g., by the ASNU assay. In one aspect, the variants of the present invention have at least 20%, e.g., at least 40%, at least 50%, at least 60%, at least 70%, at least 80%, at least 90%, at least 95%, or at least 100% of the asparaginase activity of the mature polypeptide of SEQ ID NO: 2.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has asparaginase activity. In one aspect, a fragment contains at least 300 amino acid residues, at least 325 amino acid residues or at least 350 amino acid residues.

Glucoamylases (glucan 1,4-α-glucosidase, EC 3.2.1.3) are a group of enzymes, which catalyze the hydrolysis of terminal (1→4)-linked α-D-glucose residues successively from non-reducing ends of the chains with release of β-D-glucose.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication. Improved property: The term "improved property" means a characteristic associated with a variant that is improved compared to the parent. Such improved properties include, but are not limited to, catalytic efficiency, specific activity, substrate binding, storage stability, chemical stability, oxidation stability, temperature optimum, pH optimum, pH stability, lower product inhibition, activity in the presence of ions, e.g., NaCl, activity in the presence of sugar or sugar alcohol, e.g., xylitol, tetramer stability and thermostability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 20 to 378 of SEQ ID NO: 2 based on SignalP (Nielsen et al., 1997, *Protein Engineering* 10: 1-6) that predicts amino acids 1 to 19 of SEQ ID NO: 2 are a signal peptide. In a preferred aspect, the mature polypeptide is amino acids 27 to 378 of SEQ ID NO: 2 based on N-terminal sequencing. In another aspect, the mature polypeptide is amino acids 27-378, 30-378, 75-378 or 80-378 of SEQ ID NO: 2 based on N-terminal sequencing. In another aspect, the mature polypeptide is amino acids 80-378 of SEQ ID NO: 2. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having asparaginase activity. In one aspect, the mature polypeptide coding sequence is nucleotides 58 to 1134 of SEQ ID NO: 1 based on SignalP (Nielsen et al., 1997, supra) that predicts nucleotides 1 to 57 of SEQ ID NO: 1 encode a signal peptide. In a preferred aspect, the mature polypeptide coding sequence is nucleotides 79 to 1134 of SEQ ID NO: 1 based on N-terminal sequencing of the asparaginase encoded. In another aspect, the mature polypeptide coding sequence is nucleotides 79-1134, 88-1134, 223-1134 or 238-1134 of SEQ ID NO: 1 based on N-terminal sequencing of the asparaginase encoded.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent asparaginase: The term "parent" or "parent asparaginase" means an asparaginase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having asparaginase activity. In one aspect, a subsequence contains at least 900 nucleotides, at least 975 nucleotides, or at least 1050 nucleotides.

Tm: In the context of the present invention, the term "Tm" (melting temperature) means the temperature corresponding to the apex of the signal in a thermogram as measured by Differential Scanning calorimetery (DSC) using 20 mM sodium acetate, pH 5.0, as dialysis buffer. Preferably, the DSC is performed as in Example 7. Tm (melting temperature) may also be referred to as Td (thermal denaturation temperature).

Variant: The term "variant" means a polypeptide having asparaginase activity comprising an alteration, i.e., a substitution, insertion, and/or deletion, at one or more (e.g., several) positions.

A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the asparaginase activity of the mature polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type asparaginase: The term "wild-type" asparaginase means an asparaginase expressed by a naturally occurring microorganism, such as a bacterium, yeast, or filamentous fungus found in nature.

Conventions for Designation of Variants

For purposes of the present invention, the mature polypeptide disclosed in SEQ ID NO: 2 is used to determine the corresponding amino acid residue in another asparaginase. The amino acid sequence of another asparaginase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another asparaginase can be determined by an alignment of multiple polypeptide sequences using several computer programs including, but no limited to, MUSCLE (multiple sequence comparison by log expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other asparaginase has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations may be separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. Alternatively, the following nomenclature for an amino acid substitution may be used: Position, substituted amino acid. Accordingly, the substitution of threonine at position 226 with alanine is designated as "226Ala" or "226A" Deletions. For an amino acid deletion, the following nomenclature is used: Original amino acid, position, *. Accordingly, the deletion of glycine at position 195 is designated as "Gly195*" or "G195*". Multiple deletions may be separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---------|----------|
| 195     | 195 195a 195b |
| G       | G - K - A |

Multiple alterations. Variants comprising multiple alterations may be separated by addition marks ("+"), e.g., "Arg170Tyr+Gly195Glu" or "R170Y+G195E" representing a substitution of arginine and glycine at positions 170 and 195 with tyrosine and glutamic acid, respectively. Different alterations. Where different alterations can be introduced at a position, the different alterations may be separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

DETAILED DESCRIPTION OF THE INVENTION

SEQ ID NO: 1 is the coding sequence of the asparaginase gene from *Aspergillus oryzae*. Based on N-terminal sequencing of the mature asparaginase encoded, nucleotides 1-78 encodes the signal sequence. SEQ ID NO: 2 is the amino acid sequence of asparaginase from *Aspergillus oryzae*. Based on N-terminal sequencing, amino acids 1-26 is the signal sequence. SEQ ID NO: 3 is the coding sequence of a gene encoding a variant of *Aspergillus oryzae* asparaginase having the following substitutions: N70K S307A A323R T327V A349Q S351A V353I. SEQ ID NO: 4 is the amino acid sequence of a variant of *Aspergillus oryzae* asparaginase having the following substitutions: N70K S307A A323R T327V A349Q S351A V353I. SEQ ID NO: 5 is the coding sequence of a gene encoding a variant of *Aspergillus oryzae* asparaginase having the following substitutions: N70K A323R T327V A349Q S351A V353I. SEQ ID NO: 6 is the amino acid sequence of a variant of

*Aspergillus oryzae* asparaginase having the following substitutions: N70K A323R T327V A349Q S351A V353I. SEQ ID NO: 10 is the amino acid sequence of asparaginase from *Aspergillus niger*.

Variants

The present invention in one aspect relates to an asparaginase variant, such as an isolated asparaginase variant, comprising a substitution at one or more positions corresponding to positions 140 or 241 of SEQ ID NO: 2, or a deletion at a position corresponding to position 27 of SEQ ID NO: 2, wherein the variant has at least 50% sequence identity to the mature polypeptide of any of SEQ ID NO: 2 or 4, and wherein the variant has asparaginase activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent asparaginase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of any of SEQ ID NO: 2 or 4.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 4.

In one embodiment, the amino acid at a position corresponding to position 140 is substituted with Ala, Arg, Asn, Asp, Cys, Gln, Glu, Gly, His, Ile, Leu, Lys, Met, Phe, Pro, Ser, Trp, Tyr, or Val, preferably with Asp. In another embodiment, the variant comprises or consists of the substitution T140D of the mature polypeptide of SEQ ID NO: 2.

In another embodiment, the amino acid at a position corresponding to position 241 is substituted with Ala, Arg, Asn, Asp, Cys, Gln, Glu, Gly, His, Ile, Leu, Lys, Met, Phe, Ser, Thr, Trp, Tyr, or Val, preferably with Glu. In another embodiment, the variant comprises or consists of the substitution P241E of the mature polypeptide of SEQ ID NO: 2.

In one embodiment, the variant comprises a deletion at positions corresponding to positions 27 and 28 of SEQ ID NO: 2.

In another embodiment, the variant comprises a deletion at positions corresponding to positions 27, 28 and 29 of SEQ ID NO: 2.

In one embodiment, the number of substitutions in the variant is 1-20, e.g., 1-10 or 1-5, such as 1, 2, 3, 4, 5, 6, 7, 8, 9 or 10 substitutions.

In one embodiment, the variant further comprises a substitution at one or more positions corresponding to positions 71, 74, 122, 139, 194, 197, 228, 238, 239, 240, 253, 258, 259, 297, 299, 314, 333, 334, 337, 338, 356, 363 or 373 of SEQ ID NO: 2, such as those described herein.

In another embodiment, the variant comprises one or more of the following substitutions: T71C, T74A, T74C, K122A, K122R, V139G, K194L, D197E, I228M, S238C, N239C, K240R, K253R, I258V, I258Y, R259C, R259V, S297V, S299A, T314A, P333L, S334P, S334W, E337S, S338G, S338W, G356D, K363R or E373H.

In one embodiment, the variant further comprises a substitution at one or more positions corresponding to positions 70, 307, 323, 327, 349, 351 or 353 of SEQ ID NO: 2.

In another embodiment, the variant further comprises one or more of the following substitutions: N70K, S307A, A323R, T327V, A349Q, S351A or V353I.

In another embodiment, the variant further comprises two or more of the following substitutions: N70K, S307A, A323R, T327V, A349Q, S351A or V353I.

In another embodiment, the variant further comprises three or more of the following substitutions: N70K, S307A, A323R, T327V, A349Q, S351A or V353I.

In another embodiment, the variant further comprises four or more of the following substitutions: N70K, S307A, A323R, T327V, A349Q, S351A or V353I.

In another embodiment, the variant further comprises five or more of the following substitutions: N70K, S307A, A323R, T327V, A349Q, S351A or V353I.

In another embodiment, the variant further comprises six or more of the following substitutions: N70K, S307A, A323R, T327V, A349Q, S351A or V353I.

In another embodiment, the variant further comprises the following substitutions: N70K, S307A, A323R, T327V, A349Q, S351A and V353I.

In one embodiment, the variant further comprises a substitution at a position corresponding to position 290.

In another embodiment, the variant further comprises the substitution K290V.

In a preferred embodiment, the variant comprises a substitution at a position corresponding to position 241 of SEQ ID NO: 2, wherein the variant has at least 50% sequence identity, such as at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant comprises the substitution 241E. In an even more preferred embodiment, the variant further comprises at least one of the following substitutions compared to SEQ ID NO: 2: 122A, 240R, 299A, 334P, 337S or 338W, preferably at least one of the following substitutions compared to SEQ ID NO: 2: 122A, 299A, 334P, 337S or 338W.

In one embodiment, the variant comprises a substitution at a position corresponding to position 237 of SEQ ID NO: 10, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 10. Preferably, the variant comprises the substitution 237E.

In a second aspect, the present invention relates to an asparaginase variant, such as an isolated asparaginase variant, comprising a substitution at one or more positions corresponding to positions 122, 140, 197, 238, 239, 240, 241, 253, 258, 259, 297 or 373 of SEQ ID NO: 2, or a deletion at one or more positions corresponding to positions 27, 28 or 29 of SEQ ID NO: 2, wherein the variant has at least 80% sequence identity to the mature polypeptide of any of SEQ ID NO: 2 or 4, and wherein the variant has asparaginase activity.

In an embodiment, the variant has sequence identity of at least 85%, e.g., at least 90%, at least 91%, at least 92%, at least 93%, at least 94%, at least 95%, at least 96%, at least 97%, at least 98%, or at least 99%, but less than 100%, to the amino acid sequence of the parent asparaginase.

In another embodiment, the variant has at least 85%, e.g., at least 90%, at least 91%, at least 92%, at least 93%, at least 94%, at least 95%, at least 96%, at least 97%, at least 98%, or at least 99%, but less than 100%, sequence identity to the mature polypeptide of any of SEQ ID NO: 2 or 4.

In another embodiment, the variant has at least 85%, e.g., at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2.

In another embodiment, the variant has at least 85%, e.g., at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 4.

In one embodiment, the variant comprises a deletion at a position corresponding to position 27 of SEQ ID NO: 2. In another embodiment, the variant comprises a deletion at positions corresponding to positions 27 and 28 of SEQ ID NO: 2. In another embodiment, the variant comprises a deletion at positions corresponding to positions 27, 28 and 29 of SEQ ID NO: 2.

In one embodiment, the number of substitutions in the variant is 1-20, e.g., 1-10 or 1-5, such as 1, 2, 3, 4, 5, 6, 7, 8, 9 or 10 substitutions.

In one embodiment, the variant comprises a substitution at two or more positions corresponding to any of positions 122, 140, 197, 238, 239, 240, 241, 253, 258, 259, 297 or 373. In another embodiment, the variant comprises a substitution at three or more positions corresponding to any of positions 122, 140, 197, 238, 239, 240, 241, 253, 258, 259, 297 or 373. In another embodiment, the variant comprises a substitution at four or more positions corresponding to positions 122, 140, 197, 238, 239, 240, 241, 253, 258, 259, 297 or 373.

In one embodiment, the variant comprises or consists of a substitution at a position corresponding to position 122. In another embodiment, the amino acid at a position corresponding to position 122 is substituted with Ala, Arg, Asn, Asp, Cys, Gln, Glu, Gly, His, Ile, Leu, Met, Phe, Pro, Ser, Thr, Trp, Tyr, or Val, preferably with Ala or Arg, most preferably with Ala. In another embodiment, the variant comprises or consists of the substitution K122A or K122R of the mature polypeptide of SEQ ID NO: 2.

In one embodiment, the variant comprises or consists of a substitution at a position corresponding to position 140. In another embodiment, the amino acid at a position corresponding to position 140 is substituted with Ala, Arg, Asn, Asp, Cys, Gln, Glu, Gly, His, Ile, Leu, Lys, Met, Phe, Pro, Ser, Trp, Tyr, or Val, preferably with Asp. In another embodiment, the variant comprises or consists of the substitution T140D of the mature polypeptide of SEQ ID NO: 2.

In one embodiment, the variant comprises or consists of a substitution at a position corresponding to position 197. In another embodiment, the amino acid at a position corresponding to position 197 is substituted with Ala, Arg, Asn, Cys, Gln, Glu, Gly, His, Ile, Leu, Lys, Met, Phe, Pro, Ser, Thr, Trp, Tyr, or Val, preferably with Glu. In another embodiment, the variant comprises or consists of the substitution D197E of the mature polypeptide of SEQ ID NO: 2.

In another embodiment, the variant comprises or consists of a substitution at a position corresponding to position 238. In another embodiment, the amino acid at a position corresponding to position 238 is substituted with Ala, Arg, Asn, Asp, Cys, Gln, Glu, Gly, His, Ile, Leu, Lys, Met, Phe, Pro, Thr, Trp, Tyr, or Val, preferably with Cys. In another embodiment, the variant comprises or consists of the substitution S238C of the mature polypeptide of SEQ ID NO: 2.

In another embodiment, the variant comprises or consists of a substitution at a position corresponding to position 239. In another embodiment, the amino acid at a position corresponding to position 239 is substituted with Ala, Arg, Asp, Cys, Gln, Glu, Gly, His, Ile, Leu, Lys, Met, Phe, Pro, Ser, Thr, Trp, Tyr, or Val, preferably with Cys. In another embodiment, the variant comprises or consists of the substitution N239C of the mature polypeptide of SEQ ID NO: 2.

In another embodiment, the variant comprises or consists of a substitution at a position corresponding to position 240. In another embodiment, the amino acid at a position corresponding to position 240 is substituted with Ala, Arg, Asn, Asp, Cys, Gln, Glu, Gly, His, Ile, Leu, Met, Phe, Pro, Ser, Thr, Trp, Tyr, or Val, preferably with Arg. In another embodiment, the variant comprises or consists of the substitution K240R of the mature polypeptide of SEQ ID NO: 2.

In another embodiment, the variant comprises or consists of a substitution at a position corresponding to position 241. In another embodiment, the amino acid at a position corresponding to position 241 is substituted with Ala, Arg, Asn, Asp, Cys, Gln, Glu, Gly, His, Ile, Leu, Lys, Met, Phe, Ser, Thr, Trp, Tyr, or Val, preferably with Glu. In another embodiment, the variant comprises or consists of the substitution P241E of the mature polypeptide of SEQ ID NO: 2.

In another embodiment, the variant comprises or consists of a substitution at a position corresponding to position 253. In another embodiment, the amino acid at a position corresponding to position 253 is substituted with Ala, Arg, Asn, Asp, Cys, Gln, Glu, Gly, His, Ile, Leu, Met, Phe, Pro, Ser, Thr, Trp, Tyr, or Val, preferably with Arg. In another embodiment, the variant comprises or consists of the substitution K253R of the mature polypeptide of SEQ ID NO: 2.

In another embodiment, the variant comprises or consists of a substitution at a position corresponding to position 258. In another embodiment, the amino acid at a position corresponding to position 258 is substituted with Ala, Arg, Asn, Asp, Cys, Gln, Glu, Gly, His, Leu, Lys, Met, Phe, Pro, Ser, Thr, Trp, Tyr, or Val, preferably with Tyr or Val. In another embodiment, the variant comprises or consists of the substitution I258Y or I258V of the mature polypeptide of SEQ ID NO: 2.

In another embodiment, the variant comprises or consists of a substitution at a position corresponding to position 259. In another embodiment, the amino acid at a position corresponding to position 259 is substituted with Ala, Asn, Asp, Cys, Gln, Glu, Gly, His, Ile, Leu, Lys, Met, Phe, Pro, Ser, Thr, Trp, Tyr, or Val, preferably with Cys or Val. In another embodiment, the variant comprises or consists of the substitution R259C or R259V of the mature polypeptide of SEQ ID NO: 2.

In another embodiment, the variant comprises or consists of a substitution at a position corresponding to position 297.

In another embodiment, the amino acid at a position corresponding to position 297 is substituted with Ala, Arg, Asn, Asp, Cys, Gln, Glu, Gly, His, Ile, Leu, Lys, Met, Phe, Pro, Thr, Trp, Tyr, or Val, preferably with Val. In another embodiment, the variant comprises or consists of the substitution S297V of the mature polypeptide of SEQ ID NO: 2.

In another embodiment, the variant comprises or consists of a substitution at a position corresponding to position 373. In another embodiment, the amino acid at a position corresponding to position 373 is substituted with Ala, Arg, Asn, Asp, Cys, Gln, Gly, His, Ile, Leu, Lys, Met, Phe, Pro, Ser, Thr, Trp, Tyr, or Val, preferably with His. In another embodiment, the variant comprises or consists of the substitution E373H of the mature polypeptide of SEQ ID NO: 2.

In one embodiment, the variant comprises or consists of a substitution at positions corresponding to positions 122 and 140, such as those described above.

In another embodiment, the variant comprises or consists of a substitution at positions corresponding to positions 122 and 197, such as those described above.

In another embodiment, the variant comprises or consists of a substitution at positions corresponding to positions 122 and 238, such as those described above.

In another embodiment, the variant comprises or consists of a substitution at positions corresponding to positions 122 and 239, such as those described above.

In another embodiment, the variant comprises or consists of a substitution at positions corresponding to positions 122 and 240, such as those described above.

In another embodiment, the variant comprises or consists of a substitution at positions corresponding to positions 122 and 241, such as those described above.

In another embodiment, the variant comprises or consists of a substitution at positions corresponding to positions 122 and 253, such as those described above.

In another embodiment, the variant comprises or consists of a substitution at positions corresponding to positions 122 and 258, such as those described above.

In another embodiment, the variant comprises or consists of a substitution at positions corresponding to positions 122 and 259, such as those described above.

In another embodiment, the variant comprises or consists of a substitution at positions corresponding to positions 122 and 297, such as those described above.

In another embodiment, the variant comprises or consists of a substitution at positions corresponding to positions 122 and 373, such as those described above.

In another embodiment, the variant comprises or consists of a substitution at positions corresponding to positions 140 and 197, such as those described above.

In another embodiment, the variant comprises or consists of a substitution at positions corresponding to positions 140 and 238, such as those described above.

In another embodiment, the variant comprises or consists of a substitution at positions corresponding to positions 140 and 239, such as those described above.

In another embodiment, the variant comprises or consists of a substitution at positions corresponding to positions 140 and 240, such as those described above.

In another embodiment, the variant comprises or consists of a substitution at positions corresponding to positions 140 and 241, such as those described above.

In another embodiment, the variant comprises or consists of a substitution at positions corresponding to positions 140 and 253, such as those described above.

In another embodiment, the variant comprises or consists of a substitution at positions corresponding to positions 140 and 258, such as those described above.

In another embodiment, the variant comprises or consists of a substitution at positions corresponding to positions 140 and 259, such as those described above.

In another embodiment, the variant comprises or consists of a substitution at positions corresponding to positions 140 and 297, such as those described above.

In another embodiment, the variant comprises or consists of a substitution at positions corresponding to positions 140 and 373, such as those described above.

In another embodiment, the variant comprises or consists of a substitution at positions corresponding to positions 197 and 238, such as those described above.

In another embodiment, the variant comprises or consists of a substitution at positions corresponding to positions 197 and 239, such as those described above.

In another embodiment, the variant comprises or consists of a substitution at positions corresponding to positions 197 and 240, such as those described above.

In another embodiment, the variant comprises or consists of a substitution at positions corresponding to positions 197 and 241, such as those described above.

In another embodiment, the variant comprises or consists of a substitution at positions corresponding to positions 197 and 253, such as those described above.

In another embodiment, the variant comprises or consists of a substitution at positions corresponding to positions 197 and 258, such as those described above.

In another embodiment, the variant comprises or consists of a substitution at positions corresponding to positions 197 and 259, such as those described above.

In another embodiment, the variant comprises or consists of a substitution at positions corresponding to positions 197 and 297, such as those described above.

In another embodiment, the variant comprises or consists of a substitution at positions corresponding to positions 197 and 373, such as those described above.

In another embodiment, the variant comprises or consists of a substitution at positions corresponding to positions 238 and 239, such as those described above.

In another embodiment, the variant comprises or consists of a substitution at positions corresponding to positions 238 and 240, such as those described above.

In another embodiment, the variant comprises or consists of a substitution at positions corresponding to positions 238 and 241, such as those described above.

In another embodiment, the variant comprises or consists of a substitution at positions corresponding to positions 238 and 253, such as those described above.

In another embodiment, the variant comprises or consists of a substitution at positions corresponding to positions 238 and 258, such as those described above.

In another embodiment, the variant comprises or consists of a substitution at positions corresponding to positions 238 and 259, such as those described above.

In another embodiment, the variant comprises or consists of a substitution at positions corresponding to positions 238 and 297, such as those described above.

In another embodiment, the variant comprises or consists of a substitution at positions corresponding to positions 238 and 373, such as those described above.

In another embodiment, the variant comprises or consists of a substitution at positions corresponding to positions 239 and 240, such as those described above.

In another embodiment, the variant comprises or consists of a substitution at positions corresponding to positions 239 and 241, such as those described above.

In another embodiment, the variant comprises or consists of a substitution at positions corresponding to positions 239 and 253, such as those described above.

In another embodiment, the variant comprises or consists of a substitution at positions corresponding to positions 239 and 258, such as those described above.

In another embodiment, the variant comprises or consists of a substitution at positions corresponding to positions 239 and 259, such as those described above.

In another embodiment, the variant comprises or consists of a substitution at positions corresponding to positions 239 and 297, such as those described above.

In another embodiment, the variant comprises or consists of a substitution at positions corresponding to positions 239 and 373, such as those described above.

In another embodiment, the variant comprises or consists of a substitution at positions corresponding to positions 240 and 241, such as those described above.

In another embodiment, the variant comprises or consists of a substitution at positions corresponding to positions 240 and 253, such as those described above.

In another embodiment, the variant comprises or consists of a substitution at positions corresponding to positions 240 and 258, such as those described above.

In another embodiment, the variant comprises or consists of a substitution at positions corresponding to positions 240 and 259, such as those described above.

In another embodiment, the variant comprises or consists of a substitution at positions corresponding to positions 240 and 297, such as those described above.

In another embodiment, the variant comprises or consists of a substitution at positions corresponding to positions 240 and 373, such as those described above.

In another embodiment, the variant comprises or consists of a substitution at positions corresponding to positions 241 and 253, such as those described above.

In another embodiment, the variant comprises or consists of a substitution at positions corresponding to positions 241 and 258, such as those described above.

In another embodiment, the variant comprises or consists of a substitution at positions corresponding to positions 241 and 259, such as those described above.

In another embodiment, the variant comprises or consists of a substitution at positions corresponding to positions 241 and 297, such as those described above.

In another embodiment, the variant comprises or consists of a substitution at positions corresponding to positions 241 and 373, such as those described above.

In another embodiment, the variant comprises or consists of a substitution at positions corresponding to positions 253 and 258, such as those described above.

In another embodiment, the variant comprises or consists of a substitution at positions corresponding to positions 253 and 259, such as those described above.

In another embodiment, the variant comprises or consists of a substitution at positions corresponding to positions 253 and 297, such as those described above.

In another embodiment, the variant comprises or consists of a substitution at positions corresponding to positions 253 and 373, such as those described above.

In another embodiment, the variant comprises or consists of a substitution at positions corresponding to positions 258 and 259, such as those described above.

In another embodiment, the variant comprises or consists of a substitution at positions corresponding to positions 258 and 297, such as those described above.

In another embodiment, the variant comprises or consists of a substitution at positions corresponding to positions 258 and 373, such as those described above.

In another embodiment, the variant comprises or consists of a substitution at positions corresponding to positions 259 and 297, such as those described above.

In another embodiment, the variant comprises or consists of a substitution at positions corresponding to positions 259 and 373, such as those described above.

In another embodiment, the variant comprises or consists of a substitution at positions corresponding to positions 297 and 373, such as those described above.

In one embodiment, the variant further comprises a substitution at one or more positions corresponding to positions 71, 74, 139, 194, 228, 299, 314, 333, 334, 337, 338, 356 or 363 of SEQ ID NO: 2.

In one embodiment, the variant further comprises a substitution at one or more positions corresponding to positions 70, 307, 323, 327, 349, 351 or 353 of SEQ ID NO: 2.

In another embodiment, the variant further comprises one or more of the following substitutions: N70K, S307A, A323R, T327V, A349Q, S351A or V353I.

In another embodiment, the variant further comprises two or more of the following substitutions: N70K, S307A, A323R, T327V, A349Q, S351A or V353I.

In another embodiment, the variant further comprises three or more of the following substitutions: N70K, S307A, A323R, T327V, A349Q, S351A or V353I.

In another embodiment, the variant further comprises four or more of the following substitutions: N70K, S307A, A323R, T327V, A349Q, S351A or V353I.

In another embodiment, the variant further comprises five or more of the following substitutions: N70K, S307A, A323R, T327V, A349Q, S351A or V353I.

In another embodiment, the variant further comprises six or more of the following substitutions: N70K, S307A, A323R, T327V, A349Q, S351A or V353I.

In another embodiment, the variant further comprises the following substitutions: N70K, S307A, A323R, T327V, A349Q, S351A and V353I.

In one embodiment, the variant further comprises a substitution at a position corresponding to position 290.

In another embodiment, the variant further comprises the substitution K290V.

In a preferred embodiment, the variant comprises a substitution at a position corresponding to position 122 of SEQ ID NO: 2, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant comprises the substitution 122A. In an even more preferred embodiment, the variant further comprises at least one of the following substitutions compared to SEQ ID NO: 2: 240R, 241E, 299A, 334P, 337S or 338W, preferably at least one of the following substitutions compared to SEQ ID NO: 2: 241E, 299A, 334P, 337S or 338W.

In a preferred embodiment, the variant comprises a substitution at a position corresponding to position 240 of SEQ ID NO: 2, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant comprises the substitution 240R. In an even more preferred embodiment, the variant further comprises at least one of the following substitutions compared to SEQ ID NO: 2: 122A, 241E, 299A, 334P, 337S or 338W.

In one embodiment, the variant comprises a substitution at a position corresponding to position 118 of SEQ ID NO: 10, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 10. Preferably, the variant comprises the substitution 118A.

In a third aspect, the present invention relates to an asparaginase variant, such as an isolated asparaginase variant, comprising (i) one or more of the following substitutions, wherein each position corresponds to a position in SEQ ID NO: 2: a substitution of the amino acid at position 71 with Cys, position 74 with Cys, position 122 with Ala, position 139 with Gly, position 140 with Asp, position 194 with Leu, position 197 with Glu, position 238 with Cys, position 239 with Cys, position 240 with Arg, position 241 with Glu, position 253 with Arg, position 258 with Tyr, position 259 with Cys or Val, position 334 with Trp, position 338 with Trp, position 356 with Asp, position 363 with Arg, or position 373 with His, or (ii) a deletion at a position corresponding to position 27 of SEQ ID NO: 2; wherein the variant has at least 50% sequence identity to the mature polypeptide of any of SEQ ID NO: 2 or 4, and wherein the variant has asparaginase activity.

In a preferred embodiment, the variant comprises (i) one or more of the following substitutions, wherein each position corresponds to a position in SEQ ID NO: 2: T71C, T74C, K122A, V139G, T140D, K194L, D197E, S238C, N239C, K240R, P241E, K253R, I258Y, R259C, R259V, S334W, S338W, G356D, K363R or E373H, or (ii) a deletion at a position corresponding to position 27 of SEQ ID NO: 2; wherein the variant has at least 50% sequence identity to the mature polypeptide of any of SEQ ID NO: 2 or 4, and wherein the variant has asparaginase activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent asparaginase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, sequence identity to the mature polypeptide of any of SEQ ID NO: 2 or 4.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2.

In another embodiment, the variant has at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 4.

In one embodiment, the variant comprises a deletion at a position corresponding to position 27 of SEQ ID NO: 2. In another embodiment, the variant comprises a deletion at positions corresponding to positions 27 and 28 of SEQ ID NO: 2. In another embodiment, the variant comprises a deletion at positions corresponding to positions 27, 28 and 29 of SEQ ID NO: 2.

In one embodiment, the number of substitutions in the variant is 1-20, e.g., 1-10 or 1-5, such as 1, 2, 3, 4, 5, 6, 7, 8, 9 or 10 substitutions.

In one embodiment, the variant comprises at least two of the following substitutions: a substitution of the amino acid at position 71 with Cys, position 74 with Cys, position 122 with Ala, position 139 with Gly, position 140 with Asp, position 194 with Leu, position 197 with Glu, position 238 with Cys, position 239 with Cys, position 240 with Arg, position 241 with Glu, position 253 with Arg, position 258 with Tyr, position 259 with Cys or Val, position 334 with Trp, position 338 with Trp, position 356 with Asp, position 363 with Arg, or position 373 with His. In another embodiment, the variant comprises at least two of the following substitutions: T71C, T74C, K122A, V139G, T140D, K194L, D197E, S238C, N239C, K240R, P241E, K253R, I258Y, R259C, R259V, S334W, S338W, G356D, K363R or E373H.

In another embodiment, the variant comprises at least three of the following substitutions: a substitution of the amino acid at position 71 with Cys, position 74 with Cys, position 122 with Ala, position 139 with Gly, position 140 with Asp, position 194 with Leu, position 197 with Glu, position 238 with Cys, position 239 with Cys, position 240 with Arg, position 241 with Glu, position 253 with Arg, position 258 with Tyr, position 259 with Cys or Val, position 334 with Trp, position 338 with Trp, position 356 with Asp, position 363 with Arg, or position 373 with His. In another embodiment, the variant comprises at least three of the following substitutions: T71C, T74C, K122A, V139G, T140D, K194L, D197E, S238C, N239C, K240R, P241E, K253R, I258Y, R259C, R259V, S334W, S338W, G356D, K363R or E373H.

In another embodiment, the variant comprises at least four of the following substitutions: a substitution of the amino acid at position 71 with Cys, position 74 with Cys, position 122 with Ala, position 139 with Gly, position 140 with Asp, position 194 with Leu, position 197 with Glu, position 238 with Cys, position 239 with Cys, position 240 with Arg, position 241 with Glu, position 253 with Arg, position 258 with Tyr, position 259 with Cys or Val, position 334 with Trp, position 338 with Trp, position 356 with Asp, position 363 with Arg, or position 373 with His. In another embodiment, the variant comprises at least four of the following substitutions: T71C, T74C, K122A, V139G, T140D, K194L, D197E, S238C, N239C, K240R, P241E, K253R, I258Y, R259C, R259V, S334W, S338W, G356D, K363R or E373H.

In one embodiment, the variant further comprises a substitution at one or more positions corresponding to positions 228, 297, 299, 314, 333 or 337 of SEQ ID NO: 2.

In another embodiment, the variant further comprises one or more of the following substitutions: I228M, S297V, S299A, T314A, P333L or E337S.

In one embodiment, the variant further comprises a substitution at one or more positions corresponding to positions 70, 307, 323, 327, 349, 351 or 353 of SEQ ID NO: 2.

In another embodiment, the variant further comprises one or more of the following substitutions: N70K, S307A, A323R, T327V, A349Q, S351A or V353I.

In another embodiment, the variant further comprises two or more of the following substitutions: N70K, S307A, A323R, T327V, A349Q, S351A or V353I.

In another embodiment, the variant further comprises three or more of the following substitutions: N70K, S307A, A323R, T327V, A349Q, S351A or V353I.

In another embodiment, the variant further comprises four or more of the following substitutions: N70K, S307A, A323R, T327V, A349Q, S351A or V353I.

In another embodiment, the variant further comprises five or more of the following substitutions: N70K, S307A, A323R, T327V, A349Q, S351A or V353I.

In another embodiment, the variant further comprises six or more of the following substitutions: N70K, S307A, A323R, T327V, A349Q, S351A or V353I.

In another embodiment, the variant further comprises the following substitutions: N70K, S307A, A323R, T327V, A349Q, S351A and V353I.

In one embodiment, the variant further comprises a substitution at a position corresponding to position 290.

In another embodiment, the variant further comprises the substitution K290V.

In a preferred embodiment, the variant comprises the substitution 122A compared to SEQ ID NO: 2, wherein the variant has at least 50% sequence identity, such as at least 55%, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant further comprises at least one of the following substitutions compared to SEQ ID NO: 2: 240R, 241E, 299A, 334P, 337S or 338W, preferably at least one of the following substitutions compared to SEQ ID NO: 2: 241E, 299A, 334P, 337S or 338W.

In a preferred embodiment, the variant comprises the substitution 240R compared to SEQ ID NO: 2, wherein the variant has at least 50% sequence identity, such as at least 55%, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant further comprises at least one of the following substitutions compared to SEQ ID NO: 2: 122A, 241E, 299A, 334P, 337S or 338W.

In a preferred embodiment, the variant comprises the substitution 338W compared to SEQ ID NO: 2, wherein the variant has at least 50% sequence identity, such as at least 55%, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant further comprises at least one of the following substitutions compared to SEQ ID NO: 2: 122A, 240R, 241E, 299A, 334P or 337S, preferably at least one of the following substitutions compared to SEQ ID NO: 2: 122A, 241E, 299A, 334P or 337S.

In one embodiment, the variant comprises the substitution 334W compared to SEQ ID NO: 10, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 10.

In a fourth aspect, the present invention relates to an asparaginase variant, such as an isolated asparaginase variant, comprising (i) one or more of the following substitutions, wherein each position corresponds to a position in SEQ ID NO: 2: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H, or (ii) a deletion at one or more positions corresponding to positions 27, 28 or 29 of SEQ ID NO: 2; wherein the variant has at least 80% sequence identity to the mature polypeptide of any of SEQ ID NO: 2 or 4, and wherein the variant has asparaginase activity. In an embodiment, the variant has sequence identity of at least 85%, e.g., at least 90%, at least 91%, at least 92%, at least 93%, at least 94%, at least 95%, at least 96%, at least 97%, at least 98%, or at least 99%, but less than 100%, to the amino acid sequence of the parent asparaginase.

In another embodiment, the variant has at least 85%, e.g., at least 90%, at least 91%, at least 92%, at least 93%, at least 94%, at least 95%, at least 96%, at least 97%, at least 98%, or at least 99%, but less than 100%, sequence identity to the mature polypeptide of any of SEQ ID NO: 2 or 4.

In another embodiment, the variant has at least 85%, e.g., at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 2.

In another embodiment, the variant has at least 85%, e.g., at least 90%, at least 91%, at least 92%, at least 93%, at least 94%, at least 95%, at least 96%, at least 97%, at least 98%, or at least 99%, but less than 100%, sequence identity to the mature polypeptide of SEQ ID NO: 4.

In one embodiment, the variant comprises a deletion at a position corresponding to position 27 of SEQ ID NO: 2. In another embodiment, the variant comprises a deletion at positions corresponding to positions 27 and 28 of SEQ ID NO: 2. In another embodiment, the variant comprises a deletion at positions corresponding to positions 27, 28 and 29 of SEQ ID NO: 2.

In one embodiment, the number of substitutions in the variant is 1-20, e.g., 1-10 or 1-5, such as 1, 2, 3, 4, 5, 6, 7, 8, 9 or 10 subsitutions.

In one embodiment, the variant comprises at least two of the following substitutions: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H. In another embodiment, the variant comprises at least three of the following substitutions: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H. In another embodiment, the variant comprises at least four of the following substitutions: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H.

In one embodiment, the variant comprises or consists of the substitution T71C.

In another embodiment, the variant comprises or consists of the substitution T74A.

In another embodiment, the variant comprises or consists of the substitution T74C.

In another embodiment, the variant comprises or consists of the substitution K122A.

In another embodiment, the variant comprises or consists of the substitution K122R.

In another embodiment, the variant comprises or consists of the substitution V139G.

In another embodiment, the variant comprises or consists of the substitution T140D.

In another embodiment, the variant comprises or consists of the substitution K194L.

In another embodiment, the variant comprises or consists of the substitution D197E.

In another embodiment, the variant comprises or consists of the substitution I228M.

In another embodiment, the variant comprises or consists of the substitution S238C.

In another embodiment, the variant comprises or consists of the substitution N239C.

In another embodiment, the variant comprises or consists of the substitution K240R.

In another embodiment, the variant comprises or consists of the substitution P241E.

In another embodiment, the variant comprises or consists of the substitution K253R.

In another embodiment, the variant comprises or consists of the substitution I258V.

In another embodiment, the variant comprises or consists of the substitution I258Y.

In another embodiment, the variant comprises or consists of the substitution R259C.

In another embodiment, the variant comprises or consists of the substitution R259V.

In another embodiment, the variant comprises or consists of the substitution S297V.

In another embodiment, the variant comprises or consists of the substitution S299A.

In another embodiment, the variant comprises or consists of the substitution T314A.

In another embodiment, the variant comprises or consists of the substitution P333L.

In another embodiment, the variant comprises or consists of the substitution S334P.

In another embodiment, the variant comprises or consists of the substitution S334W.

In another embodiment, the variant comprises or consists of the substitution E337S.

In another embodiment, the variant comprises or consists of the substitution S338G.

In another embodiment, the variant comprises or consists of the substitution S338W.

In another embodiment, the variant comprises or consists of the substitution G356D.

In another embodiment, the variant comprises or consists of the substitution K363R.

In another embodiment, the variant comprises or consists of the substitution E373H.

In one embodiment, the variant comprises one or more of the following substitutions: K122A, K240R, P241E, S299A, S334P, E337S or S338W.

In another embodiment, the variant comprises two or more of the following substitutions: K122A, K240R, P241E, S299A, S334P, E337S or S338W.

In another embodiment, the variant comprises three or more of the following substitutions: K122A, K240R, P241E, S299A, S334P, E337S or S338W.

In one embodiment, the variant further comprises a substitution at one or more positions corresponding to positions 70, 307, 323, 327, 349, 351 or 353 of SEQ ID NO: 2.

In another embodiment, the variant further comprises one or more of the following substitutions: N70K, S307A, A323R, T327V, A349Q, S351A or V353I.

In another embodiment, the variant further comprises two or more of the following substitutions: N70K, S307A, A323R, T327V, A349Q, S351A or V353I.

In another embodiment, the variant further comprises three or more of the following substitutions: N70K, S307A, A323R, T327V, A349Q, S351A or V353I.

In another embodiment, the variant further comprises four or more of the following substitutions: N70K, S307A, A323R, T327V, A349Q, S351A or V353I.

In another embodiment, the variant further comprises five or more of the following substitutions: N70K, S307A, A323R, T327V, A349Q, S351A or V353I.

In another embodiment, the variant further comprises six or more of the following substitutions: N70K, S307A, A323R, T327V, A349Q, S351A or V353I.

In another embodiment, the variant further comprises the following substitutions: N70K, S307A, A323R, T327V, A349Q, S351A and V353I.

In one embodiment, the variant further comprises a substitution at a position corresponding to position 290.

In another embodiment, the variant further comprises the substitution K290V.

In a preferred embodiment, the variant comprises the substitution 299A compared to SEQ ID NO: 2, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant further comprises at least one of the following substitutions compared to SEQ ID NO: 2: 122A, 240R, 241E, 334P, 337S or 338W, preferably at least one of the following substitutions compared to SEQ ID NO: 2: 122A, 241E, 334P, 337S or 338W.

In a preferred embodiment, the variant comprises the substitution 334P compared to SEQ ID NO: 2, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant further comprises at least one of the following substitutions compared to SEQ ID NO: 2: 122A, 240R, 241E, 299A, 337S or 338W, preferably at least one of the following substitutions compared to SEQ ID NO: 2: 122A, 241E, 299A, 337S or 338W.

In a preferred embodiment, the variant comprises the substitution 337S compared to SEQ ID NO: 2, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 4. In a more preferred embodiment, the variant further comprises at least one of the following substitutions compared to SEQ ID NO: 2: 122A, 240R, 241E, 299A, 334P or 338W, preferably at least one of the following substitutions compared to SEQ ID NO: 2: 122A, 241E, 299A, 334P or 338W.

In a fifth aspect, the present invention relates to an asparaginase variant, such as an isolated asparaginase variant, having a melting temperature Tm of at least 76° C., preferably at least 77° C., at least 78° C., at least 79° C. or at least 80° C., e.g., at least 82° C., at least 83° C., at least 84° C. or at least 85° C., where the Tm is determined by Differential Scanning calorimetry, and having at least 50% sequence identity to the mature polypeptide of any of SEQ ID NO: 2 or 4.

In a sixth aspect, the present invention relates to an asparaginase variant, such as an isolated asparaginase variant, comprising the substitution 286V compared to SEQ ID NO: 10, wherein the variant has at least 80% sequence identity, such as at least 85%, e.g., at least 90%, at least 91%, at least 92%, at least 93%, at least 94%, at least 95%, at least 96%, at least 97%, at least 98%, or at least 99%, but less than 100% sequence identity, to the mature polypeptide of SEQ ID NO: 10.

The variants of the present invention according to any of the aspects disclosed above, may further comprise one or more additional alterations, such as one or more additional substitutions, at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for asparaginase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The variants of the present invention according to any of the aspects disclosed above, may consist of 325 to 375, e.g., 330 to 370, 335 to 365 or 340 to 360, amino acids.

The variants of the present invention according to any of the aspects disclosed above, may have an improved property compared to the parent enzyme. Or they may have an improved property compared to asparaginase enzymes of the prior art. Such an improved property will typically be one which is relevant if the variant were to be used as set out below, for example in a method for producing a food product or in a method of producing a fermentation product from a starch-containing material.

A variant which exhibits a property which is improved compared to the parent asparaginase is one which demonstrates a measurable reduction or increase in the relevant property, typically such that the variant is more suited to use as set out below, for example in a method for producing a food product or in a method of producing a fermentation product from a starch-containing material.

In an embodiment, the variant has improved catalytic efficiency, i.e., higher kcat, compared to the parent enzyme. This will allow for use of a smaller amount of the variant in a method for producing a food product as compared to the amount of parent asparaginase required.

In an embodiment, the variant has a higher kcat at higher temperature, compared to the parent enzyme.

In an embodiment, the variant has improved specific activity compared to the parent enzyme. Specific activity in the context of the present invention means the asparaginase activity measured in units per mg of pure protein. Asparaginase activity may be determined according to one of the asparaginase activity assays described in the Examples, e.g., by the ASNU assay.

In an embodiment, the variant has improved substrate binding, i.e., lower Km, compared to the parent enzyme.

In an embodiment, the variant has improved storage stability compared to the parent enzyme. By improved storage stability is meant an improved stability under storage conditions.

In an embodiment, the variant has improved chemical stability compared to the parent enzyme.

In an embodiment, the variant has improved oxidation stability compared to the parent enzyme.

In an embodiment, the variant has a higher temperature optimum compared to the parent enzyme.

In an embodiment, the variant has a decreased pH optimum compared to the parent enzyme. More particularly, it may be a pH optimum which is more suited for use in a method for producing a food product.

In an embodiment, the variant has improved pH stability compared to the parent enzyme.

In an embodiment, the variant has a lower product inhibition compared to the parent enzyme.

In an embodiment, the activity of the variant is different in the presence of ions, e.g., NaCl compared to the parent enzyme.

In an embodiment, the activity of the variant is different in the presence of sugar or sugar alcohol, e.g., xylitol compared to the parent enzyme.

In an embodiment, the variant has improved tetramer stability compared to the parent enzyme.

In a preferred embodiment, a variant of the present invention, according to any of the aspects disclosed above, has an improved thermostability relative to the parent.

In a preferred embodiment, a variant of the present invention, according to any of the aspects disclosed above, has an improved thermostability relative to the asparaginase encoded by SEQ ID NO: 2.

In another preferred embodiment, a variant of the present invention, according to any of the aspects disclosed above, has an improved thermostability relative to the asparaginase encoded by SEQ ID NO: 4.

The thermostability may be determined as the residual asparaginase activity after heat treatment divided by the asparaginase activity without heat treatment. Heat treatment may be incubation at or around, e.g., pH 4, pH 5, pH 6 or pH 7 at a high temperature for, e.g., 10, 20, 40, 60, 120 or 240 minutes. The asparaginase activity without heat treatment may in this context be determined as the asparaginase activity of a sample which has been incubated at 4° C. in the same buffer and for the same time as the sample which is heat treated, or it may be the asparaginase activity before heat treatment.

The residual asparaginase activity may be determined as described in Example 3 of the present application.

The polypeptides of the present invention may show a residual asparaginase activity of at least 40%, such as at least 50%, at least 60%, at least 70%, at least 80% or at least 90%, after incubation in 0.5% sodium acid pyrophosphate (SAPP) at pH 5 at high temperature for a period of time, e.g., 240 minutes, compared to the asparaginase activity without heat treatment.

High temperature in the context of the present invention may mean, e.g., 60° C., 65° C., 70° C., 71° C., 72° C., 73° C., 74° C., 75° C., 76° C., 77° C., 78° C., 79° C. or 80° C.

In a preferred embodiment, thermostability is determined as the residual asparaginase activity after heat treatment divided by the asparaginase activity without heat treatment, where heat treatment is incubation at pH 5 at 70-80° C. for 240 minutes, and where the asparaginase activity without heat treatment is determined as the asparaginase activity of a sample which has been incubated at 4° C. in the same buffer and for the same time as the sample which is heat treated.

In a preferred embodiment, a variant of the present invention, according to any of the aspects disclosed above, has a residual activity after 4 hours' incubation in deionised water with 0.5% SAPP at 70° C., pH 5, of at least 20%, preferably at least 40%, more preferably at least 60%, even more preferably at least 80%, of the activity without such incubation. The asparaginase activity may be determined by the rASNU assay as described in the Examples. It may be determined at pH 6 and at 37° C.

In another preferred embodiment, a variant of the present invention according to any of the aspects disclosed above, has a residual activity after 4 hours' incubation in deionised water with 0.5% SAPP at 72° C., pH 5, of at least 5%, preferably at least 10%, more preferably at least 20%, even more preferably at least 40%, such as at least 60% or at least 80%, of the activity without such incubation.

In another preferred embodiment, a variant of the present invention according to any of the aspects disclosed above, has a residual activity after 4 hours' incubation in deionized water with 0.5% SAPP at 74° C., pH 5, of at least 1%, preferably at least 5%, more preferably at least 10%, even more preferably at least 20%, such as at least 40% or at least 60%, of the activity without such incubation.

In another preferred embodiment, a variant of the present invention according to any of the aspects disclosed above, has an activity at 35° C., pH 6, of at least 20%, preferably at least 30%, more preferably at least 35%, of its activity at 50° C., pH 6.

In another preferred embodiment, a variant of the present invention according to any of the aspects disclosed above, has an activity at 70° C., pH 6, of at least 20%, preferably at least 25%, more preferably at least 30%, of its activity at 50° C., pH 6.

In another preferred embodiment, a variant of the present invention according to any of the aspects disclosed above, has (i) an activity at 35° C., pH 6, of at least 20%, preferably at least 30%, more preferably at least 35%, of its activity at 50° C., pH 6, and (ii) an activity at 70° C., pH 6, of at least 20%, preferably at least 25%, more preferably at least 30%, of its activity at 50° C., pH 6.

In another preferred embodiment, a variant of the present invention according to any of the aspects disclosed above, has an activity at pH 5 of at least 20%, preferably at least 30%, more preferably at least 40%, even more preferably at least 50%, of its activity at pH 6.5. The activity may be determined at 50° C.

In another preferred embodiment, a variant of the present invention according to any of the aspects disclosed above, has (i) an activity at 35° C., pH 6, of at least 20%, preferably at least 30%, more preferably at least 35%, of its activity at 50° C., pH 6, (ii) an activity at 70° C., pH 6, of at least 20%, preferably at least 25%, more preferably at least 30%, of its activity at 50° C., pH 6, and (iii) an activity at pH 5, 50° C., of at least 20%, preferably at least 30%, more preferably at least 40%, even more preferably at least 50%, of its activity at pH 6.5, 50° C.

In another preferred embodiment, a variant of the present invention according to any of the aspects disclosed above, has a residual activity after 2 hours' incubation in deionised water with 0.5% SAPP at pH 4 and 70° C. of at least 20%, preferably at least 30%, more preferably at least 40%, even more preferably at least 50%, of the activity without such incubation.

The thermostability may be determined by Differential Scanning calorimetry (DSC) as the melting temperature Tm. The DSC assay may be performed as described in Example 7. In a preferred embodiment, a variant of the present invention, according to any of the aspects disclosed above, has a melting temperature Tm of at least 76° C., preferably at least 77° C., at least 78° C., at least 79° C. or at least 80° C., where the Tm is determined by Differential Scanning calorimetry. In another preferred embodiment, a variant of the present invention, according to any of the aspects disclosed above, has a melting temperature Tm of at least 82° C., at least 83° C., at least 84° C. or at least 85° C., where the Tm is determined by Differential Scanning calorimetry.

The thermostability may be determined in a Thermal Shift Assay (TSA) as the melting temperature Tm. The TSA assay may be performed as described in Example 6. In a preferred embodiment, a variant of the present invention, according to any of the aspects disclosed above, has a melting temperature Tm of at least 72° C., preferably at least 73° C., at least 74° C. or at least 75° C., where the Tm is determined by TSA. In another preferred embodiment, a variant of the present invention, according to any of the aspects disclosed above, has a melting temperature Tm of at least 76° C., at least 77° C., at least 78° C., at least 79° C. or at least 80° C., where the Tm is determined by TSA.

Parent Asparaginases

The parent asparaginase may be (a) a polypeptide having at least 60% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, or (ii) the full-length complement of (i); or (c) a polypeptide encoded by a polynucleotide having at least 60% sequence identity to the mature polypeptide coding sequence of SEQ ID NO: 1.

In an embodiment, the parent is a polypeptide having asparaginase activity which has a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one embodiment, the amino acid sequence of the parent differs by no more than 10 amino acids, e.g., 1, 2, 3, 4, 5, 6, 7, 8, 9 or 10, from the mature polypeptide of SEQ ID NO: 2.

In another embodiment, the parent comprises or consists of the amino acid sequence of SEQ ID NO: 2. In another embodiment, the parent comprises or consists of the mature polypeptide of SEQ ID NO: 2. In another embodiment, the parent comprises or consists of amino acids 27 to 378 of SEQ ID NO: 2.

In another embodiment, the parent is a fragment of the mature polypeptide of SEQ ID NO: 2 containing at least 320 amino acid residues, e.g., at least 340 or at least 360 amino acid residues.

In another embodiment, the parent is an allelic variant of the mature polypeptide of SEQ ID NO: 2.

In another embodiment, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is the mature polypeptide coding sequence of SEQ ID NO: 1. In another embodiment, the nucleic acid probe is nucleotides 79 to 1134 of SEQ ID NO: 1. In another embodiment, the nucleic acid probe is a polynucleotide that encodes the polypeptide of SEQ ID NO: 2; the mature polypeptide thereof; or a fragment thereof. In another embodiment, the nucleic acid probe is SEQ ID NO: 1.

In another embodiment, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The parent asparaginase may be (a) a polypeptide having at least 60% sequence identity to the mature polypeptide of SEQ ID NO: 4; (b) a polypeptide encoded by a polynucleotide that hybridizes under low stringency conditions with (i) the mature polypeptide coding sequence of SEQ ID NO: 3, or (ii) the full-length complement of (i); or (c) a polypeptide encoded by a polynucleotide having at least 60% sequence identity to the mature polypeptide coding sequence of SEQ ID NO: 3.

In an embodiment, the parent is a polypeptide having asparaginase activity which has a sequence identity to the mature polypeptide of SEQ ID NO: 4 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In one embodiment, the amino acid sequence of the parent differs by no more than 10 amino acids, e.g., 1, 2, 3, 4, 5, 6, 7, 8, 9 or 10, from the mature polypeptide of SEQ ID NO: 4.

In another embodiment, the parent comprises or consists of the amino acid sequence of SEQ ID NO: 4. In another embodiment, the parent comprises or consists of the mature polypeptide of SEQ ID NO: 4. In another embodiment, the parent comprises or consists of amino acids 27 to 378 of SEQ ID NO: 4.

In another embodiment, the parent is a fragment of the mature polypeptide of SEQ ID NO: 4 containing at least 320 amino acid residues, e.g., at least 340 or at least 360 amino acid residues.

In another embodiment, the parent is an allelic variant of the mature polypeptide of SEQ ID NO: 4.

In another embodiment, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 3, or (ii) the full-length complement of (i) (Sambrook et al., 1989, *Molecular Cloning, A Laboratory Manual*, 2d edition, Cold Spring Harbor, N.Y.).

In another embodiment, the parent is encoded by a polynucleotide having a sequence identity to the mature polypeptide coding sequence of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The parent may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one embodiment, the parent is secreted extracellularly.

The parent may be a fungal asparaginase. It may be a filamentous fungal asparaginase such as an *Acremonium, Agaricus, Alternaria, Aspergillus, Aureobasidium, Botryosphaeria, Botryotinia, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neosartorya, Neurospora, Paecilomyces, Penicillium, Phanerochaete, Piromyces, Poitrasia, Pseudoplectania, Pseudotrichonympha, Rhizomucor, Schizophyllum, Sclerotinia, Scytalidium, Talaromyces, Thermoascus, Thielavia, Tolypocladium, Trichoderma, Trichophaea, Verticillium, Volvariella,* or *Xylaria* asparaginase.

In one embodiment, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Aspergillus terreus, Botryotinia fuckeliana, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neosartorya fischeri, Neurospora crassa, Penicillium chrysogenum, Penicillium citrinum, Penicillium funiculosum, Penicillium purpurogenum, Phanerochaete chrysosporium, Sclerotinia sclerotiorum, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* asparaginase.

In one embodiment, the parent is an *Aspergillus oryzae* asparaginase, e.g., the asparaginase of SEQ ID NO: 2 or the mature polypeptide thereof.

In another embodiment, the parent is an *Aspergillus niger* asparaginase, e.g., the asparaginase disclosed in WO 2004/030468.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to a method for obtaining an asparaginase variant, comprising introducing into a parent asparaginase a substitution at one or more positions corresponding to positions 122, 140, 197, 241, 253 or 373 of the mature polypeptide of SEQ ID NO: 2, wherein the variant has asparaginase activity; and recovering the variant.

Preferably, the parent asparaginase has at least 50% sequence identity to the mature polypeptide of any of SEQ ID NO: 2 or 4, such as at least 60, at least 70 or at least 80% sequence identity to the mature polypeptide of any of SEQ ID NO: 2 or 4, more preferably at least 85, at least 90, at least 95 or at least 98% sequence identity to the mature polypeptide of any of SEQ ID NO: 2 or 4.

In another aspect, the invention relates to a method for obtaining an asparaginase variant, comprising introducing into a parent asparaginase, which has at least 80% sequence identity to the mature polypeptide of any of SEQ ID NO: 2 or 4, a substitution at one or more positions corresponding to positions 122, 140, 197, 238, 239, 240, 241, 253, 258, 259, 297 or 373 of SEQ ID NO: 2, wherein the variant has asparaginase activity; and recovering the variant.

Preferably, the parent asparaginase has at least 85, at least 90, at least 95 or at least 98% sequence identity to the mature polypeptide of any of SEQ ID NO: 2 or 4.

In another aspect, the invention relates to a method for obtaining an asparaginase variant, comprising introducing into a parent asparaginase one or more of the following substitutions, wherein each position corresponds to a position in SEQ ID NO: 2: a substitution of the amino acid at position 71 with Cys, position 74 with Cys, position 122 with Ala or Arg, position 139 with Gly, position 140 with Asp, position 194 with Leu, position 197 with Glu, position 238 with Cys, position 239 with Cys, position 240 with Arg, position 241 with Glu, position 253 with Arg, position 258 with Tyr, position 259 with Cys or Val, position 299 with Ala, position 334 with Trp, position 338 with Trp, position 356 with Asp, position 363 with Arg, or position 373 with His, wherein the variant has asparaginase activity; and recovering the variant.

In a preferred embodiment, the method comprises introducing into a parent asparaginase one or more of the following substitutions, wherein each position corresponds to a position in SEQ ID NO: 2: T71C, T74C, K122A, K122R, V139G, T140D, K194L, D197E, I228M, S238C, N239C, K240R, P241E, K253R, I258Y, R259C, R259V, S299A, S334W, S338W, G356D, K363R or E373H, wherein the variant has asparaginase activity; and recovering the variant.

Preferably, the parent asparaginase has at least 50% sequence identity to the mature polypeptide of any of SEQ ID NO: 2 or 4, such as at least 60, at least 70 or at least 80% sequence identity to the mature polypeptide of any of SEQ ID NO: 2 or 4, more preferably at least 85, at least 90, at least 95 or at least 98% sequence identity to the mature polypeptide of any of SEQ ID NO: 2 or 4.

In another aspect, the invention relates to a method for obtaining an asparaginase variant, comprising introducing into a parent asparaginase, which has at least 80% sequence identity to the mature polypeptide of any of SEQ ID NO: 2 or 4, one or more of the following substitutions, wherein each position corresponds to a position in SEQ ID NO: 2: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H, wherein the variant has asparaginase activity; and recovering the variant.

Preferably, the parent asparaginase has at least 85, at least 90, at least 95 or at least 98% sequence identity to the mature polypeptide of any of SEQ ID NO: 2 or 4.

For all of the above aspects, the variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides, such as isolated polynucleotides, encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*.

Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative embodiment, the variant is not recovered, but rather a host cell of the present invention expressing the variant is used as a source of the variant.

Fermentation Broth Formulations or Cell Compositions

The present invention also relates to a fermentation broth formulation or a cell composition comprising a variant of the present invention. The fermentation broth product further comprises additional ingredients used in the fermentation process, such as, for example, cells (including, the host cells containing the gene encoding the variant of the present invention which are used to produce the variant of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a variant of the present invention. Preferably, the compositions are enriched in such a variant. The term "enriched" indicates that the asparaginase activity of the composition has been increased, e.g., with an enrichment factor of at least 1.1.

The compositions may comprise a variant of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The asparaginase variants according to the invention or compositions comprising such asparaginase variants can be used in the production of a food product. In one embodiment, a variant of the present invention or a composition comprising such variant is used to reduce the amount of acrylamide formed in a thermally processed food product based on an asparagine-containing raw material.

In one embodiment, the present invention relates to a method for producing a food product from a food material, comprising (i) adding a variant of the present invention to the food material, and (ii) heating the enzyme treated food material. The variant is to be added to the food material in an amount that is effective in reducing the level of asparagine present in the food material. This will result in less acrylamide being formed in the heating step which is to take place after the enzyme treatment. Such methods are disclosed, e.g., in WO 2004/026043. The methods disclosed in WO 2004/026043 and all preferences disclosed are incorporated by reference.

The food material which is to be treated with a variant of the invention may be any raw material which is to be included in the food product or it may be any intermediate form of the food product which occurs during the production process prior to obtaining the final form of the food product. It may be any individual raw material used and/or any mixture thereof and/or any mixture thereof also including additives and/or processing aids, and/or any subsequently processed form thereof. For example, for the food product bread, the food material may comprise for example wheat, wheat flour, the initial mixture thereof with other bread ingredients such as for example water, salt, yeast and bread improving compositions, the mixed dough, the kneaded dough, the leavened dough and the partially baked dough. For example for some potato-based food products, e.g., potato snacks or croquettes, the food material may be potato mash or dehydrated potato flakes or granules. For other potato-based food products, such as sliced potato chips or French fries, the food material may be potato pieces which have optionally been peeled, blanched and/or dried. For tortilla chips, the food material may be corn masa. For breakfast cereals, the food material may be, e.g., whole wheat flour, oat flour, corn flour, wheat kernels, oat kernels or oat flakes. For coffee-based food products, the food material may be the green coffee beans.

The food product may be made from at least one raw material that is of plant origin, for example potato, coffee, cocoa, rice, cereal, for example wheat, rye corn, maize, barley, groats, buckwheat and oat. Also food products made from more than one raw material are included in the scope of this invention, for example food products comprising both wheat (e.g., in the form of wheat flour) and potato. The method of the invention may be suitable for producing, e.g., a cereal based product, such as bread, pastry, cake, pretzels, bagels, Dutch honey cake, cookies, gingerbread, gingercake, breakfast cereals or crispbread; a vegetable based product, e.g., a potato based product, such as French fries, sliced potato chips, dough-based potato snacks, fabricated potato products or croquettes; or a coffee based product.

Raw materials as cited above are known to contain substantial amounts of asparagine which is involved in the formation of acrylamide during the heating step of the production process. Alternatively, the asparagine may originate from other sources than the raw materials, e.g., from protein hydrolysates, such as yeast extracts, soy hydrolysate, casein hydrolysate or the like, which are used as an additive in the food production process. A preferred production process is the production of potato products, such as potato snacks, sliced potato chips or French fries, which includes deep-frying or baking. Another preferred production process is the production of breakfast cereals, which includes toasting. Another preferred production process is the baking of bread and other baked products from wheat flour and/or flours from other cereal origin.

The variant, which is preferably a thermostable variant, may be added to the food material at elevated temperature, e.g., at 40-80° C., such as 50-75° C. or 60-70° C.

After the enzyme treatment, the enzyme treated food material is subjected to a heat treatment. The heat treatment is a part of the method for producing from the food material (i.e., the raw material or the intermediate form of the food product) a food product. In a conventional method, i.e., a method without asparaginase treatment, more acrylamide would be formed during the heat treatment as compared to the method of the invention where some of the asparagine of the food material is hydrolysed by the asparaginase variant.

Preferred heating steps are those at which at least a part of an intermediate form of the food product, e.g., the surface of the food product, is exposed to temperatures at which the formation of acrylamide is promoted, e.g. 110° C. or higher, or 120° C. or higher. The heating step in the method according to the invention may be carried out in ovens, for instance at a temperature of 180-220° C. such as for the baking of bread and other bakery products, or in oil such as the frying of potato chips or French fries, for example at 160-190° C.

Food products obtained by a method of the invention are characterized by significantly reduced acrylamide levels in comparison with equivalent food products obtainable by a production method that does not comprise adding an asparaginase in an amount that is effective in reducing the level of asparagine involved in the formation of acrylamide during a heating step.

The method according to the invention can be used to obtain a decrease of the acrylamide content of the produced food product of more than 25%, preferably more than 30% or more than 40%, more preferably more than 50%, compared to a food product obtained with a similar process not comprising asparaginase treatment.

In another aspect, the invention provides food products obtainable by a method of the invention as described above.

In another aspect, the invention relates to the use of an asparaginase variant as described hereinbefore to produce food products.

The asparaginase variants according to the invention may also be employed in the therapy of tumors. The metabolism of tumour cells requires L-asparagine, which can quickly be degraded by asparaginases. The asparaginase variants according to the invention can be used as an adjunct in treatment of some human leukaemia. Administration of asparaginase in experimental animals and humans leads to regression of certain lymphomas and leukemia. Therefore in one embodiment, the invention relates to an asparaginase of the invention or a composition comprising such variant for use as medicament, e.g., in the treatment of tumors, e.g., in the treatment of lymphomas or leukaemia in animals or humans.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germ plasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

Processes for Producing Fermentation Products, Dextrins, and Sugars from Starch-Containing Materials The present invention also relates to a process of producing a fermentation product, comprising:
(a) liquefying a starch-containing material to a dextrin with an alpha-amylase in the presence of an asparaginase of the invention;
(b) saccharifying the dextrin to a sugar with a saccharifying enzyme; and
(c) fermenting the sugar using a fermenting organism to produce the fermentation product.

The present invention also relates to a process of producing a sugar, comprising:
(a) liquefying a starch-containing material to a dextrin with an alpha-amylase in the presence of an asparaginase of the invention; and
(b) saccharifying the dextrin to a sugar with a saccharifying enzyme.

The present invention also relates to a process of producing a dextrin, comprising
(a) liquefying a starch-containing material to the dextrin with an alpha-amylase in the presence of an asparaginase of the invention; and
(b) recovering the dextrin.

The present invention also relates to a process of producing a fermentation product, comprising:
(a) treating a starch-containing material with an asparaginase of the invention;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.

The present invention also relates to a process of producing a sugar, comprising:
(a) treating a starch-containing material with an asparaginase of the invention;
(b) liquefying the treated starch-containing material to a dextrin with an alpha-amylase; and
(c) saccharifying the dextrin to a sugar with a saccharifying enzyme.

The present invention also relates to a process of producing a dextrin, comprising:
(a) treating a starch-containing material with an asparaginase of the invention; and
(b) liquefying the treated starch-containing material to a dextrin with an alpha-amylase.

Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolyzate is used in the production of, e.g., syrups. Both dry and wet milling are well known in the art of starch processing and may be used in a process of the invention. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The starch-containing material may be used to produce a sugar, a dextrin, or a fermentation product. Generally, the sugar-containing material is liquefied to a dextrin with an alpha-amylase, which is then followed by saccharification (a process which converts the dextrin to a sugar) and fermentation (a process which converts the sugar to a fermentation product).

In an embodiment, the starch-containing material is treated with an asparaginase of the invention prior to liquefaction. This treatment may be carried out at any pH and temperature suitable for enzyme activity for a period of time to allow for the enzymatic reaction to take place. In an embodiment, the temperature is in the range of 20-90° C., e.g., 20-65° C. or 40-60° C.; the pH is in the range of 4.5-6.5; and the period of time is in the range of 5 minutes-2 hours, e.g., 5 minutes-1 hour.

In an embodiment, an asparaginase is added to the starch-containing material prior to liquefaction.

In an embodiment, an asparaginase of the invention is added during liquefaction.

Liquefaction is carried out in the presence of an alpha-amylase, preferably a bacterial alpha-amylase and/or acid fungal alpha-amylase. In an embodiment, a phytase is also present during liquefaction.

During a typical liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 77-86° C., 80-85° C., or 83-85° C.) and an alpha-amylase(s) is (are) added to initiate liquefaction (thinning). The liquefaction process is carried out at 85° C. for 1-2 hours. The pH is generally between 5.5 and 6.2. In order to ensure optimal enzyme stability under these conditions, 1 mM of calcium is optionally added (to provide about 40 ppm free calcium ions). After such treatment, the liquefied starch will have a "dextrose equivalent" (DE) of 10-15.

The slurry may be subsequently jet-cooked at between 95-140° C., e.g., 105-125° C., for about 1-15 minutes, e.g., about 3-10 minutes, especially around 5 minutes. The slurry is then cooled to 60-95° C. and more alpha-amylase(s) is (are) added to obtain the final hydrolysis (secondary liquefaction). The jet-cooking process is carried out at pH 4.5-6.5, typically at a pH between 5 and 6. The alpha-amylase may be added as a single dose, e.g., before jet cooking.

Saccharification may be carried out using conditions well known in the art with a glucoamylase or a beta-amylase and optionally a debranching enzyme, such as an isoamylase or a pullulanase. For instance, a full saccharification step may last from about 24 to about 72 hours, however, it is also common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (SSF), in which there is no holding stage for the saccharification, meaning that a fermenting organism, such as yeast, and enzyme(s) are added together. SSF is typically carried out at a temperature of 20-40° C., e.g., 26-34° C., preferably around 32° C., when the fermentation organism is yeast, such as a strain of *Saccharomyces cerevisiae*, and the fermentation product is ethanol.

Other fermentation products may be fermented at conditions and temperatures well known to persons skilled in the art, suitable for the fermenting organism in question. The temperature may be adjusted up or down during fermentation.

The dextrin may be recovered by methods well known in the art.

The sugar may be recovered by methods well known in the art.

The fermentation product may be recovered by methods well known in the art, e.g., by distillation.

In a particular embodiment, the process of the invention further comprises, prior to the conversion of a starch-containing material to dextrins and/or the treatment of the starch-containing material with an asparaginase of the invention, the steps of:

(x) reducing the particle size of the starch-containing material; and (y) forming a slurry comprising the starch-containing material and water.

Methods for reducing the particle size of the starch containing material are known to those skilled in the art. In an embodiment, the starch-containing material is milled to reduce the particle size.

The aqueous slurry may contain from 10-55 wt. % dry solids (DS), preferably 25-45 wt. % dry solids (DS), more preferably 30-40 wt. % dry solids (DS) of starch-containing material.

Processes for Producing Fermentation Products from Ungelatinized Starch-Containing Materials The present invention also relates to a process for producing a fermentation product from a starch-containing material without gelatinization (often referred to as "without cooking") of the starch-containing material. In an embodiment, the process includes saccharifying the (e.g., milled) starch-containing material below the initial gelatinization temperature, preferably in the presence of an alpha-amylase and/or a carbohydrate-source generating enzyme(s) (saccharifying enzyme(s)) to produce sugars that can be fermented into the fermentation product by a fermenting organism.

Accordingly, this aspect of the invention relates to a process of producing a fermentation product, comprising converting a starch-containing material to a dextrin with an alpha-amylase; saccharifying the dextrin to a sugar with a glucoamylase; and fermenting the sugar using a fermenting organism in the presence of an asparaginase of the invention in a single step at a temperature below the initial gelatinization temperature of the starch-containing material.

The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. The initial gelatinization temperature of a given starch-containing material may be determined as the temperature at which birefringence is lost in 5% of the starch granules using the method described by Gorinstein and Lii, 1992, *Starch/Stärke* 44(12): 461-466.

The process of the present invention may further comprise recovering the fermentation product, e.g., by distillation.

The starch-containing material may be a slurry, such as granular starch, having 10-55 wt. % dry solids (DS), preferably 25-45 wt. % dry solids, more preferably 30-40 wt. % dry solids of starch-containing material may be prepared. The slurry may include water and/or process waters, such as stillage (backset), scrubber water, evaporator condensate or distillate, side-stripper water from distillation, or process water from other fermentation product plants. Because the process is carried out below the initial gelatinization temperature and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like.

The starch-containing material may be prepared by reducing the particle size, preferably by dry or wet milling, to 0.05-3.0 mm, preferably 0.1-0.5 mm. After being subjected to a method or process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the dry solids in the starch-containing material is converted into a soluble starch hydrolyzate.

The process of this aspect of the invention is conducted at a temperature below the initial gelatinization temperature, e.g., a temperature in the range between 25-40° C., such as 25-40° C., 29-35° C., 30-34° C., such as around 32° C. One skilled in the art can easily determine suitable process conditions.

The process of the invention may be carried out at a pH from about 3 and 7, e.g., 3.5 to 6 or pH 4 to 5.

In an embodiment fermentation is carried out so that the sugar level, such as glucose level, is kept at a low level, such as below 6 wt. %, below about 3 wt. %, below about 2 wt. %, below about 1 wt. %, below about 0.5 wt. %, below 0.25% wt. %, or below about 0.1 wt. %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt. %, such as below about 0.2 wt. %.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley.

Production of Fermentation Products and Sugars from a Plant Extract

The present invention also relates to a process of producing a sugar and/or a fermentation product such as ethanol, from a plant extract containing amino acid(s) and soluble sugar(s) (e.g., fructose, galactose, glucose, maltose, sucrose, and/or oligomers thereof), e.g., sugarcane, comprising applying an asparaginase of the invention to the plant extract.

In particular, the present invention relates to a process of producing a fermentation product, comprising (a) treating a plant extract containing amino acid(s) and soluble sugar(s) with an asparaginase of the invention;

(b) producing molasses from the plant extract;

(c) diluting the molasses; and (d) fermenting the diluted molasses with a fermenting organism to produce ethanol.

The present invention also relates to a process of producing a fermentation product, comprising (a) treating a plant extract containing amino acid(s) and soluble sugar(s) with an asparaginase of the invention; and (b) fermenting the treated plant extract with a fermenting organism to produce the fermentation product.

The present invention also relates to a process of producing a sugar, comprising (a) treating a plant extract containing amino acid(s) and soluble sugar(s) with an asparaginase of the invention; and (b) recovering the sugar from the treated plant extract.

The present invention also relates to a process of producing sucrose, comprising:

(a) treating a plant extract containing amino acid(s) and soluble sugar(s) with an an asparaginase of the invention;

(b) clarification of the plant extract;

(c) concentration of sugars found in the clarified plant extract (e.g., by evaporation) to form a syrup containing sucrose;

(d) crystallization of sucrose from the syrup; and (e) recovering sucrose.

The sugar may be any sugar including but not limited to fructose, galactose, glucose, maltose, or sucrose.

Sugarcane is any of 6 to 37 species of tall perennial grasses of the genus *Saccharum* (family Poaceae, tribe Andropogoneae). Traditionally, sugarcane processing requires two stages. Mills extract raw sugar from freshly harvested cane, and sometimes bleach the sugar to make "mill white" sugar for local consumption. Refineries then produce refined white sugar, which is 99% sucrose.

The mill washes, chops, and uses revolving knives to shred the cane. Shredded cane is repeatedly mixed with water and crushed between rollers called crushers or diffusers to produce raw sugarcane juice. The raw sugarcane juice contains 10-15% sucrose, and the remaining fibrous solids, called bagasse, are burned for fuel. The cane juice is next mixed with lime to adjust its pH to 7. This mixing arrests sucrose's decay into glucose and fructose, and precipitates some impurities. The mixture then sits, allowing the lime and other suspended solids to settle, resulting in clarified juice. Other methods for clarifying sugarcane juice such as sulfitation and carbonation are known in the art. The clarified juice is concentrated in a multiple-effect evaporator to make a syrup containing about 60 wt. % sucrose. This syrup is further concentrated under vacuum until it becomes supersaturated, and then seeded with crystalline sugar. On cooling, more sugar crystallizes from the syrup. A centrifuge separates sucrose from the molasses. Additional crystallizations extract more sucrose; the final residue is called blackstrap.

After clarification, water is removed from the sugarcane juice by a multistep evaporation process. The leftover from this process, not viable for sucrose extraction, is called molasses and is commonly used as a substrate for fuel ethanol production.

In a process of the present invention, the plant extract is treated with an asparaginase of the invention, and molasses is produced from the treated plant extract. Molasses is produced by clarification of the plant extract; concentration of sugars found in the clarified plant extract (e.g., by evaporation) to form a syrup; and crystallization of sucrose from the syrup to form the molasses. The molasses is then diluted, e.g., with water or plant extract juice (e.g., sugarcane juice), and the diluted molasses is fermented to produce a fermentation product.

The plant extract may be treated with an asparaginase of the invention in any step prior to evaporation. For example, the plant extract may be treated with an asparaginase of the invention during juice extraction, crushing, juice recovery, and/or juice clarification. Thus, the asparaginase may be added during the milling process and/or in the clarification steps.

The process of the present invention may further comprise recovering the fermentation product.

The process of the present invention may further comprise recovering the sugar. The sugar may be recovered by any process known in the art. For example, sucrose may be recovered by a process comprising (x) clarification of the plant extract;

(y) concentration of sugars found in the clarified plant extract (e.g., by evaporation) to form a syrup; and (z) crystallization of sucrose from the syrup.

As explained above, typically, mills run the raw juice clarification for sugar and/or ethanol at a pH of around 7 to minimize Maillard product formation. Another benefit of the process of the present invention is that the raw juice may be clarified for sugar and/or ethanol production at a more alkaline pH such as a pH of 7.5-9, e.g., 8-9. By using an asparaginase of the invention to avoid Maillard product formation, a higher pH can be used, which improves the clarification performance in terms of quality (sugar brightness and/or juice lighter), yield (decreases the amount of sugar which is lost in the refinery process) and productivity (decreases the clarification hold time).

The plant extract may be sweet sorghum, sugar beets, sugar cane, or any mixture thereof. In particular, the plant extract may be raw sugarcane juice or clarified sugarcane juice.

Fermentation Products

The term "fermentation product" means a product produced by a process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., H2 and CO2); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer.

Fermenting Organisms

The term "fermenting organism" refers to any organism, including bacterial and fungal organisms, such as yeast and filamentous fungi, suitable for producing a desired fermentation product. Suitable fermenting organisms according to the invention are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast. Preferred yeast include strains of *Saccharomyces*, in particular *Saccharomyces cerevisiae* or *Saccharomyces uvarum*; strains of *Pichia*, in particular *Pichia stipitis* such as *Pichia stipitis* CBS 5773 or *Pichia pastoris*; strains of *Candida*, in particular *Candida arabinofermentans, Candida boidinii, Candida diddensii, Candida shehatae, Candida sonorensis, Candida tropicalis*, or *Candida utilis*. Other fermenting organisms include strains of *Hansenula*, in particular *Hansenula anomala* or *Hansenula po/ymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of Zymobacter, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1L1 (*Appl. Microbiol. Biotech.* 77: 61-86), Thermoanarobacter ethanolicus, *Thermoanaerobacter mathranii*, or *Thermoanaerobacter thermosaccharolyticum*. Strains of *Lactobacillus* are also envisioned as are strains of *Corynebacterium glutamicum* R, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

Commercially available yeast include LNF SA-1, LNF BG-1, LNF PE-2, and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

According to the invention the fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may according to the invention be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Enzymes

The enzyme(s) described below are to be used in an "effective amount" in the processes of the present invention.

Asparaginases

The asparaginase may be an enzyme of EC 3.5.1.1 (asparaginase or L-asparagine amidohydrolase).

In one preferred aspect, the asparaginase is an asparaginase variant comprising a substitution at one or more positions corresponding to positions 140 or 241 of SEQ ID NO: 2, or a deletion at a position corresponding to position 27 of SEQ ID NO: 2, wherein the variant has at least 50% sequence identity to the mature polypeptide of any of SEQ ID NO: 2 or 4, and wherein the variant has asparaginase activity.

In another preferred aspect, the asparaginase is an asparaginase variant comprising a substitution at one or more positions corresponding to positions 122, 140, 197, 238, 239, 240, 241, 253, 258, 259, 297 or 373 of SEQ ID NO: 2, or a deletion at one or more positions corresponding to positions 27, 28 or 29 of SEQ ID NO: 2, wherein the variant has at least 80% sequence identity to the mature polypeptide of any of SEQ ID NO: 2 or 4, and wherein the variant has asparaginase activity.

In another preferred aspect, the asparaginase is an asparaginase variant comprising (i) one or more of the following substitutions, wherein each position corresponds to a position in SEQ ID NO: 2: a substitution of the amino acid at position 71 with Cys, position 74 with Cys, position 122 with Ala, position 139 with Gly, position 140 with Asp, position 194 with Leu, position 197 with Glu, position 238 with Cys, position 239 with Cys, position 240 with Arg, position 241 with Glu, position 253 with Arg, position 258 with Tyr, position 259 with Cys or Val, position 334 with Trp, position 338 with Trp, position 356 with Asp, position 363 with Arg, or position 373 with His, or (ii) a deletion at a position corresponding to position 27 of SEQ ID NO: 2; wherein the variant has at least 50% sequence identity to the mature polypeptide of any of SEQ ID NO: 2 or 4, and wherein the variant has asparaginase activity.

Preferably, the variant comprises (i) one or more of the following substitutions, wherein each position corresponds to a position in SEQ ID NO: 2: T71C, T74C, K122A, V139G, T140D, K194L, D197E, S238C, N239C, K240R, P241E, K253R, I258Y, R259C, R259V, S334W, S338W, G356D, K363R or E373H, or (ii) a deletion at a position corresponding to position 27 of SEQ ID NO: 2; wherein the variant has at least 50% sequence identity to the mature polypeptide of any of SEQ ID NO: 2 or 4, and wherein the variant has asparaginase activity.

In another preferred aspect, the asparaginase is an asparaginase variant comprising (i) one or more of the following substitutions, wherein each position corresponds to a position in SEQ ID NO: 2: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H, or (ii) a deletion at one or more positions corresponding to positions 27, 28 or 29 of SEQ ID NO: 2; wherein the variant has at least 80% sequence identity to the mature polypeptide of any of SEQ ID NO: 2 or 4, and wherein the variant has asparaginase activity.

In another preferred aspect, the asparaginase is an asparaginase variant having a melting temperature Tm of at least 76° C., preferably at least 77° C., at least 78° C., at least 79° C. or at least 80° C., e.g., at least 82° C., at least 83° C., at least 84° C. or at least 85° C., where the Tm is determined by Differential Scanning calorimetry, and having at least 50% sequence identity to the mature polypeptide of any of SEQ ID NO: 2 or 4.

Alpha-Amylases

According to the invention any alpha-amylase may be used, such as of fungal, bacterial or plant origin. In a preferred embodiment the alpha-amylase is an acid alpha-amylase, e.g., acid fungal or acid bacterial alpha-amylase. The term "acid alpha-amylase" means an alpha-amylase (EC 3.2.1.1) which added in an effective amount has activity optimum at a pH in the range of 3 to 7, preferably from 3.5 to 6, or more preferably from 4-5.

Bacterial Alpha-Amylases

An alpha-amylase for use in the present invention may be a bacterial alpha-amylase, e.g., derived from *Bacillus*. In a preferred embodiment the *Bacillus* alpha-amylase is derived from a strain of *Bacillus amyloliquefaciens*, *Bacillus licheniformis*, *Bacillus stearothermophilus*, or *Bacillus subtilis*, but may also be derived from other *Bacillus* sp.

Specific examples of alpha-amylases include the *Bacillus amyloliquefaciens* alpha-amylase of SEQ ID NO: 5 in WO 99/19467, the *Bacillus licheniformis* alpha-amylase of SEQ ID NO: 4 in WO 99/19467, and the *Bacillus stearothermophilus* alpha-amylase of SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NO: 3, 4 or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acids at positions R179 to G182, preferably a double deletion disclosed in WO 96/23873—see, e.g., page 20, lines 1-10 (hereby incorporated by reference), preferably corresponding to delta(181-182) compared to the amino acid sequence of *Bacillus stearothermophilus* alpha-amylase set forth in SEQ ID NO: 3 disclosed in WO 99/19467 or the deletion of amino acids R179 and G180 using SEQ ID NO: 3 in WO 99/19467 for numbering (which reference is hereby incorporated by reference). Even more preferred are *Bacillus* alpha-amylases, especially *Bacillus stearothermophilus* alpha-amylases, which have a double deletion corresponding to delta(181-182) and further comprise a N193F substitution (also denoted 1181*+G182*+N193F) compared to the wild-type BSG alpha-amylase amino acid sequence set forth in SEQ ID NO: 3 disclosed in WO 99/19467.

Bacterial Hybrid Alpha-Amylases

The alpha-amylase may be a hybrid alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment, the bacterial alpha-amylase is dosed in an amount of 0.0005-5 KNU per g DS (dry solids), preferably 0.001-1 KNU per g DS, such as around 0.050 KNU per g DS.

Fungal Alpha-Amylases

Fungal alpha-amylases include alpha-amylases derived from a strain of *Aspergillus*, such as, *Aspergillus kawachii*, *Aspergillus niger* and *Aspergillus oryzae* alpha-amylases.

A preferred acidic fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain of *Aspergillus niger*. In a preferred embodiment the acid fungal alpha-amylase is an *Aspergillus niger* alpha-amylase disclosed as "AMYA_ASPNG" in the Swiss-prot/TeEMBL database under the primary accession no. P56271 and described in WO 89/01969 (Example 3—incorporated by reference). An acid fungal alpha-amylase derived from *Aspergillus niger* is SP288 (available from Novozymes A/S, Denmark).

Other wild-type alpha-amylases include those derived from a strain of *Meripilus* and *Rhizomucor*, preferably a strain of *Meripilus giganteus* or *Rhizomucor pusillus* (WO 2004/055178 which is incorporated herein by reference).

In a preferred embodiment the alpha-amylase is derived from *Aspergillus kawachii* (Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL: #AB008370).

The fungal alpha-amylase may also be a wild-type enzyme comprising a starch-binding domain (SBD) and an alpha-amylase catalytic domain, or a variant thereof.

Fungal Hybrid Alpha-Amylases

In a preferred embodiment, the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain (SBD), and optionally a linker.

Examples of hybrid alpha-amylases include those disclosed in Tables 1 to 5 of the examples in WO 2006/069290 including the variant with the catalytic domain JA118 and *Athelia rolfsii* SBD (SEQ ID NO: 100 in WO 2006/069290), *Rhizomucor pusillus* alpha-amylase with *Athelia rolfsii* AMG linker and SBD (SEQ ID NO: 101 in WO 2006/069290), *Rhizomucor pusillus* alpha-amylase with *Aspergillus niger* glucoamylase linker and SBD (which is disclosed in Table 5 as a combination of amino acid sequences SEQ ID NO: 20, SEQ ID NO: 72 and SEQ ID NO: 96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO: 102 in WO 2006/069290). Other hybrid alpha-amylases are listed in Tables 3, 4, 5, and 6 in Example 4 in U.S. application Ser. No. 11/316,535 and WO 2006/069290 (which are hereby incorporated by reference).

Other examples of hybrid alpha-amylases include those disclosed in U.S. Patent Application Publication No. 2005/0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

An acid alpha-amylase may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

Commercial Alpha-Amylase Products

Preferred commercial compositions comprising alpha-amylase include MYCOLASE™ (DSM), BAN™, TERMAMYL™ SC, FUNGAMYL™, LIQUOZYME™ X, LIQUOZYME™ SC and SAN™ SUPER, SAN™ EXTRA L (Novozymes A/S) and CLARASE™ L-40,000, DEX-LO™, SPEZYME™ FRED, SPEZYME™ AA, SPEZYME™ ALPHA, SPEZYME™ DELTA AA, GC358, GC980, SPEZYME™ CL and SPEZYME™ RSL (Danisco A/S), and the acid fungal alpha-amylase from *Aspergillus niger* referred to as SP288 (available from Novozymes A/S, Denmark).

Carbohydrate-Source Generating Enzymes (Saccharifying Enzymes)

The term "carbohydrate-source generating enzyme" includes glucoamylase (a glucose generator), beta-amylase and maltogenic amylase (both maltose generators) and also alpha-glucosidase, isoamylase and pullulanase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Blends include mixtures comprising at least a glucoamylase and an alpha-amylase, especially an acid amylase, even more preferred an acid fungal alpha-amylase.

The ratio between glucoamylase activity (AGU) and acid fungal alpha-amylase activity (FAU-F) (i.e., AGU per FAU-F) may in a preferred embodiment of the invention be between 0.1 and 100 AGU/FAU-F, in particular between 2 and 50 AGU/FAU-F, such as in the range from 10-40 AGU/FAU-F, especially when performing a one-step fermentation (raw starch hydrolysis—RSH), i.e., when saccharification and fermentation are carried out simultaneously (i.e., without a liquefaction step).

In a conventional starch-to-ethanol process (i.e., including a liquefaction step) the ratio may preferably be as defined in EP 140410, especially when saccharification and fermentation are carried out simultaneously.

Glucoamylases

A glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in positions A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and Nagasaka et al., 1998, *Appl. Microbiol. Biotechnol.* 50: 323-330), *Talaromyces* glucoamylases, in particular derived from *Talaromyces duponti, Talaromyces emersonii* (WO 99/28448), *Talaromyces leycettanus* (U.S. Pat. No. Re. 32,153), and *Talaromyces thermophilus* (U.S. Pat. No. 4,587,215).

Other glucoamylases include glucoamylases from *Clostridium*, in particular *C. thermoamylolyticum* (EP 135138) and *C. thermohydrosulfuricum* (WO 86/01831), *Trametes cingulata, Pachykytospora papyracea*, and *Leucopaxillus giganteus*, all disclosed in WO 2006/069289; or *Peniophora rufomarginata* disclosed in PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may have a high degree of sequence identity to any of above mentioned glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available glucoamylase compositions include AMG 200L; AMG 300L; SAN™ SUPER, SAN™ EXTRA L, SPIRIZYME™ PLUS, SPIRIZYME™ FUEL, SPIRIZYME™ B4U, SPIRIZYME ULTRA™ and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Glucoamylases may be added in an amount of 0.02-20 AGU/g DS, preferably 0.1-10 AGU/g DS, especially between 1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-Amylases

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979, *Progress in Industrial Microbiology* 15: 112-115). These beta-amylases are characterized by having a temperature optimum in the range from 40° C. to 65° C. and a pH optimum in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylases

The amylase may also be a maltogenic alpha-amylase (glucan 1,4-alpha-maltohydrolase, EC 3.2.1.133), which catalyzes the hydrolysis of amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may be added in an amount of 0.05-5 mg total protein/gram DS or 0.05-5 MANU/g DS.

Phytases

Any phytase may be used in a process of the present invention. Phytases are enzymes that degrade phytates and/or phytic acid by specifically hydrolyzing the ester link between inositol and phosphorus. Phytase activity is credited with phosphorus and ion availability in many ingredients. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytase (EC 3.1.3.26)). An example of phytase is myo-inositol-hexakiphosphate-3-phosphohydrolase.

Phytases can be obtained from microorganisms such as fungal and bacterial organisms. For example, the phytase may be obtained from filamentous fungi such as *Aspergillus* (e.g., *A. ficuum, A. fumigatus, A. niger*, and *A. terreus*), *Cladospirum, Mucor* (e.g., *Mucor piriformis*), *Myceliophthora* (e.g., *M. thermophila*), *Penicillium* (e.g., *P. hordei* (ATCC No. 22053)), *P. piceum* (ATCC No. 10519), or *P. brevi-compactum* (ATCC No. 48944), *Talaromyces* (e.g., *T. thermophilus*), *Thermomyces* (WO 99/49740), and *Trichoderma* spp. (e.g., *T. reesei*).

In an embodiment, the phytate-degrading enzyme is obtained from yeast (e.g., *Arxula adeninivorans, Pichia anomala, Schwanniomyces occidentalis*), gram-negative bacteria (e.g., *Escherichia coli, Klebsiella* spp., *Pseudomonas* spp.), and gram-positive bacteria (e.g., *Bacillus* spp. such as *Bacillus subtilis*).

The phytase also may be obtained from *Citrobacter, Enterobacter,* or *Peniophora.*

In an embodiment, the phytase is derived from *Buttiauxiella* spp. such as *B. agrestis, B. brennerae, B. ferragutiase, B. gaviniae, B. izardii, B. noackiae*, and *B. warmboldiae*. In some embodiments, the phytase is a phytase disclosed in WO 2006/043178 or U.S. application Ser. No. 11/714,487.

In one preferred embodiment, the phytase has at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO: 31 of U.S. application Ser. No. 12/263,886.

Commercially-available phytases are NATUPHOS (BASF), RONOZYME P (Novozymes A/S), PHZYME (Danisco A/S, Diversa) and FINASE (AB Enzymes). The method for determining microbial phytase activity and the definition of a phytase unit is disclosed in Engelen et al., 1994, *Journal of AOAC International* 77: 760-764. The phytase may be a wild-type phytase, an active variant or active fragment thereof.

Pullulanases

Any pullulanase may be used in a process of the present invention. In an embodiment, the pullulanase is a GH57 pullulanase, e.g., a pullulanase obtained from a strain of *Thermococcus*, including *Thermococcus* sp. AM4, *Thermococcus* sp. HJ21, *Thermococcus barophilus, Thermococcus gammatolerans, Thermococcus hydrothermalis; Thermococcus kodakarensis, Thermococcus litoralis*, and *Thermococcus onnurineus*; or from a strain of *Pyrococcus*, such as *Pyrococcus abyssi* and *Pyrococcus furiosus*.

Proteases

A protease may be added during saccharification, fermentation, simultaneous saccharification and fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

The acid fungal protease may be derived from *Aspergillus, Candida, Coriolus, Endothia, Enthomophtra, Irpex, Mucor, Penicillium, Rhizopus, Sclerotium*, and *Torulopsis*. In particular, the protease may be derived from *Aspergillus aculeatus* (WO 95/02044), *Aspergillus awamori* (Hayashida et al., 1977, *Agric. Biol. Chem.* 42(5), 927-933), *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), or *Aspergillus oryzae*, such as the pepA protease; and acidic proteases from *Mucor miehei* or *Mucor pusillus*.

The protease may be a neutral or alkaline protease, such as a protease derived from a strain of *Bacillus*. A particular protease is derived from *Bacillus amyloliquefaciens* and has the sequence obtainable at Swissprot as Accession No. P06832. The proteases may have at least 90% sequence identity to the amino acid sequence disclosed in the Swissprot Database, Accession No. P06832 such as at least 92%, at least 95%, at least 96%, at least 97%, at least 98%, or particularly at least 99% identity.

The protease may have at least 90% sequence identity to the amino acid sequence disclosed as SEQ ID NO: 1 in WO 2003/048353 such as at least 92%, at least 95%, at least 96%, at least 97%, at least 98%, or particularly at least 99% identity.

The protease may be a papain-like protease selected from the group consisting of proteases within EC 3.4.22.* (cysteine protease), such as EC 3.4.22.2 (papain), EC 3.4.22.6 (chymopapain), EC 3.4.22.7 (asclepain), EC 3.4.22.14 (actinidain), EC 3.4.22.15 (cathepsin L), EC 3.4.22.25 (glycyl endopeptidase) and EC 3.4.22.30 (caricain).

In an embodiment, the protease is a protease preparation derived from a strain of *Aspergillus*, such as *Aspergillus oryzae*. In another embodiment the protease is derived from a strain of *Rhizomucor*, preferably *Rhizomucor miehei*. In another embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei*.

Aspartic acid proteases are described in, for example, Handbook of Proteolytic Enzymes, Edited by A. J. Barrett, N. D. Rawlings and J. F. Woessner, Academic Press, San Diego, 1998, Chapter 270. Examples of aspartic acid proteases include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference.

The protease also may be a metalloprotease, which is defined as a protease selected from the group consisting of:

(a) proteases belonging to EC 3.4.24 (metalloendopeptidases); preferably EC 3.4.24.39 (acid metallo proteinases);

(b) metalloproteases belonging to the M group of the above Handbook;

(c) metalloproteases not yet assigned to clans (designation: Clan MX), or belonging to either one of clans MA, MB, MC, MD, ME, MF, MG, MH (as defined at pp. 989-991 of the above Handbook);

(d) other families of metalloproteases (as defined at pp. 1448-1452 of the above Handbook);

(e) metalloproteases with a HEXXH motif;

(f) metalloproteases with an HEFTH motif;

(g) metalloproteases belonging to either one of families M3, M26, M27, M32, M34, M35, M36, M41, M43, or M47 (as defined at pp. 1448-1452 of the above Handbook);

(h) metalloproteases belonging to the M28E family; and (i) metalloproteases belonging to family M35 (as defined at pp. 1492-1495 of the above Handbook).

In other particular embodiments, metalloproteases are hydrolases in which the nucleophilic attack on a peptide bond is mediated by a water molecule, which is activated by a divalent metal cation. Examples of divalent cations are zinc, cobalt or manganese. The metal ion may be held in place by amino acid ligands. The number of ligands may be five, four, three, two, one or zero. In a particular embodiment the number is two or three, preferably three.

There are no limitations on the origin of the metalloprotease used in a process of the invention. In an embodiment the metalloprotease is classified as EC 3.4.24, preferably EC 3.4.24.39. In one embodiment, the metalloprotease is an acid-stable metalloprotease, e.g., a fungal acid-stable metalloprotease, such as a metalloprotease derived from a strain of the genus *Thermoascus*, preferably a strain of *Thermoascus aurantiacus*, especially *Thermoascus aurantiacus* CGMCC No. 0670 (classified as EC 3.4.24.39). In another embodiment, the metalloprotease is derived from a strain of the genus *Aspergillus*, preferably a strain of *Aspergillus oryzae*.

In one embodiment the metalloprotease has a degree of sequence identity to amino acids −178 to 177, −159 to 177, or preferably amino acids 1 to 177 (the mature polypeptide) of SEQ ID NO: 1 of WO 2010/008841 (a *Thermoascus aurantiacus* metalloprotease) of at least 80%, at least 82%, at least 85%, at least 90%, at least 95%, or at least 97%; and which have metalloprotease activity. In particular embodiments, the metalloprotease consists of an amino acid sequence with a degree of identity to SEQ ID NO: 1 as mentioned above.

The *Thermoascus aurantiacus* metalloprotease is a preferred example of a metalloprotease suitable for use in a process of the invention. Another metalloprotease is derived from *Aspergillus oryzae* and comprises the sequence of SEQ ID NO: 11 disclosed in WO 2003/048353, or amino acids −23-353; −23-374; −23-397; 1-353; 1-374; 1-397; 177-353; 177-374; or 177-397 thereof, and SEQ ID NO: 10 disclosed in WO 2003/048353.

Another metalloprotease suitable for use in a process of the invention is the *Aspergillus oryzae* metalloprotease comprising SEQ ID NO: 5 of WO 2010/008841, or a metalloprotease is an isolated polypeptide which has a degree of identity to SEQ ID NO: 5 of at least about 80%, at least 82%, at least 85%, at least 90%, at least 95%, or at least 97%; and which have metalloprotease activity. In particular embodiments, the metalloprotease consists of the amino acid sequence of SEQ ID NO: 5.

In a particular embodiment, a metalloprotease has an amino acid sequence that differs by forty, thirty-five, thirty, twenty-five, twenty, or by fifteen amino acids from amino acids −178 to 177, −159 to 177, or +1 to 177 of the amino acid sequences of the *Thermoascus aurantiacus* or *Aspergillus oryzae* metalloprotease.

In another embodiment, a metalloprotease has an amino acid sequence that differs by ten, or by nine, or by eight, or by seven, or by six, or by five amino acids from amino acids −178 to 177, −159 to 177, or +1 to 177 of the amino acid sequences of these metalloproteases, e.g., by four, by three, by two, or by one amino acid.

In particular embodiments, the metalloprotease a) comprises or b) consists of
  i) the amino acid sequence of amino acids −178 to 177, −159 to 177, or +1 to 177 of SEQ ID NO:1 of WO 2010/008841;
  ii) the amino acid sequence of amino acids −23-353, −23-374, −23-397, 1-353, 1-374, 1-397, 177-353, 177-374, or 177-397 of SEQ ID NO: 3 of WO 2010/008841;
  iii) the amino acid sequence of SEQ ID NO: 5 of WO 2010/008841; or allelic variants, or fragments, of the sequences of i), ii), and iii) that have protease activity.

A fragment of amino acids −178 to 177, −159 to 177, or +1 to 177 of SEQ ID NO: 1 of WO 2010/008841 or of amino acids −23-353, −23-374, −23-397, 1-353, 1-374, 1-397, 177-353, 177-374, or 177-397 of SEQ ID NO: 3 of WO 2010/008841; is a polypeptide having one or more amino acids deleted from the amino and/or carboxyl terminus of these amino acid sequences. In one embodiment a fragment contains at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

In another embodiment, the metalloprotease is combined with another protease, such as a fungal protease, preferably an acid fungal protease.

Commercially available products include ALCALASE®, ESPERASE™, FLAVOURZYME™, NEUTRASE®, RENNILASE®, NOVOZYM™ FM 2.0 L, and iZyme BA (available from Novozymes A/S, Denmark) and GC106™ and SPEZYME™ FAN from Genencor International, Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Preferred Embodiments

1. An asparaginase variant comprising a substitution at one or more positions corresponding to positions 140 or 241 of SEQ ID NO: 2, or a deletion at a position corresponding to position 27 of SEQ ID NO: 2, wherein the variant has at least 50% sequence identity to the mature polypeptide of any of SEQ ID NO: 2 or 4, and wherein the variant has asparaginase activity.

2. The variant of Embodiment 1, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to the mature polypeptide of any of SEQ ID NO: 2 or 4.

3. The variant of Embodiment 1 or 2, where the amino acid at a position corresponding to position 140 is substituted with Ala, Arg, Asn, Asp, Cys, Gln, Glu, Gly, His, Ile, Leu, Lys, Met, Phe, Pro, Ser, Trp, Tyr, or Val, preferably with Asp.

4. The variant of Embodiment 1 or 2, where the amino acid at a position corresponding to position 241 is substituted with Ala, Arg, Asn, Asp, Cys, Gln, Glu, Gly, His, Ile, Leu, Lys, Met, Phe, Ser, Thr, Trp, Tyr, or Val, preferably with Glu.

5. The variant of any of Embodiments 1-4 comprising a deletion at positions corresponding to positions 27 and 28 of SEQ ID NO: 2.

6. The variant of any of Embodiments 1-5 comprising a deletion at positions corresponding to positions 27, 28 and 29 of SEQ ID NO: 2.

7. An asparaginase variant comprising a substitution at one or more positions corresponding to positions 122, 140, 197, 238, 239, 240, 241, 253, 258, 259, 297 or 373 of SEQ ID NO: 2, or a deletion at one or more positions corresponding to positions 27, 28 or 29 of SEQ ID NO: 2, wherein the variant has at least 80% sequence identity to the mature polypeptide of any of SEQ ID NO: 2 or 4, and wherein the variant has asparaginase activity.

8. The variant of Embodiment 7, which has at least 85%, e.g., at least 90%, at least 95%, at least 96%, at least 97%, at least 98%, or at least 99%, but less than 100% sequence identity to the mature polypeptide of any of SEQ ID NO: 2 or 4.

9. The variant of Embodiment 7 or 8 comprising a substitution at one or more positions corresponding to positions 122, 240 or 241 of SEQ ID NO: 2.

10. The variant of any of Embodiments 7-9 comprising a deletion at a position corresponding to position 27 of SEQ ID NO: 2.

11. The variant of any of Embodiments 7-10 comprising a deletion at positions corresponding to positions 27 and 28 of SEQ ID NO: 2.

12. The variant of any of Embodiments 7-11 comprising a deletion at positions corresponding to positions 27, 28 and 29 of SEQ ID NO: 2.
13. The variant of any of Embodiments 7-12, where the amino acid at a position corresponding to position 122 is substituted with Ala, Arg, Asn, Asp, Cys, Gln, Glu, Gly, His, Ile, Leu, Met, Phe, Pro, Ser, Thr, Trp, Tyr, or Val, preferably with Ala or Arg, most preferably with Ala.
14. The variant of any of Embodiments 7-12, where the amino acid at a position corresponding to position 140 is substituted with Ala, Arg, Asn, Asp, Cys, Gln, Glu, Gly, His, Ile, Leu, Lys, Met, Phe, Pro, Ser, Trp, Tyr, or Val, preferably with Asp.
15. The variant of any of Embodiments 7-12, where the amino acid at a position corresponding to position 197 is substituted with Ala, Arg, Asn, Cys, Gln, Glu, Gly, His, Ile, Leu, Lys, Met, Phe, Pro, Ser, Thr, Trp, Tyr, or Val, preferably with Glu.
16. The variant of any of Embodiments 7-12, where the amino acid at a position corresponding to position 238 is substituted with Ala, Arg, Asn, Asp, Cys, Gln, Glu, Gly, His, Ile, Leu, Lys, Met, Phe, Pro, Thr, Trp, Tyr, or Val, preferably with Cys. 17. The variant of any of Embodiments 7-12, where the amino acid at a position corresponding to position 239 is substituted with Ala, Arg, Asp, Cys, Gln, Glu, Gly, His, Ile, Leu, Lys, Met, Phe, Pro, Ser, Thr, Trp, Tyr, or Val, preferably with Cys.
18. The variant of any of Embodiments 7-12, where the amino acid at a position corresponding to position 240 is substituted with Ala, Arg, Asn, Asp, Cys, Gln, Glu, Gly, His, Ile, Leu, Met, Phe, Pro, Ser, Thr, Trp, Tyr, or Val, preferably with Arg.
19. The variant of any of Embodiments 7-12, where the amino acid ata position corresponding to position 241 is substituted with Ala, Arg, Asn, Asp, Cys, Gln, Glu, Gly, His, Ile, Leu, Lys, Met, Phe, Ser, Thr, Trp, Tyr, or Val, preferably with Glu.
20. The variant of any of Embodiments 7-12, where the amino acid at a position corresponding to position 253 is substituted with Ala, Arg, Asn, Asp, Cys, Gln, Glu, Gly, His, Ile, Leu, Met, Phe, Pro, Ser, Thr, Trp, Tyr, or Val, preferably with Arg.
21. The variant of any of Embodiments 7-12, where the amino acid at a position corresponding to position 258 is substituted with Ala, Arg, Asn, Asp, Cys, Gln, Glu, Gly, His, Leu, Lys, Met, Phe, Pro, Ser, Thr, Trp, Tyr, or Val, preferably with Tyr or Val.
22. The variant of any of Embodiments 7-12, where the amino acid at a position corresponding to position 259 is substituted with Ala, Asn, Asp, Cys, Gln, Glu, Gly, His, Ile, Leu, Lys, Met, Phe, Pro, Ser, Thr, Trp, Tyr, or Val, preferably with Cys or Val.
23. The variant of any of Embodiments 7-12, where the amino acid at a position corresponding to position 297 is substituted with Ala, Arg, Asn, Asp, Cys, Gln, Glu, Gly, His, Ile, Leu, Lys, Met, Phe, Pro, Thr, Trp, Tyr, or Val, preferably with Val.
24. The variant of any of Embodiments 7-12, where the amino acid at a position corresponding to position 373 is substituted with Ala, Arg, Asn, Asp, Cys, Gln, Gly, His, Ile, Leu, Lys, Met, Phe, Pro, Ser, Thr, Trp, Tyr, or Val, preferably with His.
25. An asparaginase variant comprising (i) one or more of the following substitutions, wherein each position corresponds to a position in SEQ ID NO: 2: T71C, T74C, K122A, V139G, T140D, K194L, D197E, S238C, N239C, K240R, P241E, K253R, I258Y, R259C, R259V, S334W, S338W, G356D, K363R or E373H, or (ii) a deletion at a position corresponding to position 27 of SEQ ID NO: 2; wherein the variant has at least 50% sequence identity to the mature polypeptide of any of SEQ ID NO: 2 or 4, and wherein the variant has asparaginase activity.
26. The variant of Embodiment 25, comprising one or more of the following substitutions: K122A, K240R, P241E or S338W.
27. The variant of Embodiment 25 or 26, comprising a deletion at positions corresponding to positions 27 and 28 of SEQ ID NO: 2.
28. The variant of any of Embodiments 25-27, comprising a deletion at positions corresponding to positions 27, 28 and 29 of SEQ ID NO: 2.
29. The variant of any of Embodiments 25-28, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to the mature polypeptide of any of SEQ ID NO: 2 or 4.
30. An asparaginase variant comprising (i) one or more of the following substitutions, wherein each position corresponds to a position in SEQ ID NO: 2: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H, or (ii) a deletion at one or more positions corresponding to positions 27, 28 or 29 of SEQ ID NO: 2; wherein the variant has at least 80% sequence identity to the mature polypeptide of any of SEQ ID NO: 2 or 4, and wherein the variant has asparaginase activity.
31. The variant of Embodiment 30, comprising one or more of the following substitutions: K122A, K240R, P241E, S299A, S334P, E337S or S338W.
32. The variant of Embodiment 30 or 31, comprising a deletion at a position corresponding to position 27 of SEQ ID NO: 2.
33. The variant of any of Embodiments 30-32, comprising a deletion at positions corresponding to positions 27 and 28 of SEQ ID NO: 2.
34. The variant of any of Embodiments 30-33, comprising a deletion at positions corresponding to positions 27, 28 and 29 of SEQ ID NO: 2.
35. The variant of any of Embodiments 30-34, which has at least 85%, e.g., at least 90%, at least 95%, at least 96%, at least 97%, at least 98%, or at least 99%, but less than 100% sequence identity to the mature polypeptide of any of SEQ ID NO: 2 or 4.
36. The variant of any of Embodiments 1-35, which has an improved property relative to the parent, wherein the property is selected from the group consisting of catalytic efficiency, specific activity, substrate binding, storage stability, chemical stability, oxidation stability, temperature optimum, pH optimum, pH stability, lower product inhibition, activity in the presence of ions, e.g., NaCl, activity in the presence of sugar or sugar alcohol, e.g., xylitol, tetramer stability and thermostability.
37. The variant of any of Embodiments 1-36, which has an improved thermostability relative to the parent.
38. The variant of any of Embodiments 1-37, which has a melting temperature Tm of at least 76° C., preferably at least 77° C., at least 78° C., at least 79° C., at least 80° C., e.g., at least 82° C., at least 83° C., at least 84° C. or at least 85° C., where the Tm is determined by Differential Scanning calorimetry.

39. The variant of any of Embodiments 1-38, wherein the mature polypeptide is amino acids 27 to 378 of SEQ ID NO: 2.

40. An asparaginase variant having a melting temperature Tm of at least 76° C., preferably at least 77° C., at least 78° C., at least 79° C. or at least 80° C., e.g., at least 82° C., at least 83° C., at least 84° C. or at least 85° C., where the Tm is determined by Differential Scanning calorimetry, and having at least 50% sequence identity to the mature polypeptide of any of SEQ ID NO: 2 or 4.

41. The asparaginase variant of Embodiment 40, which has at least 60%, e.g., at least 65%, at least 70%, at least 75%, at least 80%, at least 85%, at least 90%, at least 95%, at least 96%, at least 97%, at least 98%, or at least 99%, but less than 100% sequence identity to the mature polypeptide of any of SEQ ID NO: 2 or 4.

42. The variant of any of Embodiments 1-41, which is a variant of a parent asparaginase selected from the group consisting of:
   a. a polypeptide having at least 60% sequence identity to the mature polypeptide of SEQ ID NO: 2;
   b. a polypeptide encoded by a polynucleotide that hybridizes under low stringency conditions with (i) the mature polypeptide coding sequence of SEQ ID NO: 1, or (ii) the full-length complement of (i);
   c. a polypeptide encoded by a polynucleotide having at least 60% identity to the mature polypeptide coding sequence of SEQ ID NO: 1; and
   d. a fragment of the mature polypeptide of SEQ ID NO: 2, which has asparaginase activity.

43. The variant of Embodiment 42, wherein the parent asparaginase has at least 60%, e.g., at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO: 2.

44. The variant of Embodiment 42 or 43, wherein the parent asparaginase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1 or (ii) the full-length complement of (i).

45. The variant of any of Embodiments 42-44, wherein the parent asparaginase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 1.

46. The variant of any of Embodiments 42-45, wherein the parent asparaginase comprises or consists of the mature polypeptide of SEQ ID NO: 2.

47. The variant of any of Embodiments 42-46, wherein the parent asparaginase is a fragment of the mature polypeptide of SEQ ID NO: 2, wherein the fragment has asparaginase activity.

48. The variant of any of Embodiments 1-41, which is a variant of a parent asparaginase selected from the group consisting of:
   a. a polypeptide having at least 60% sequence identity to the mature polypeptide of SEQ ID NO: 4;
   b. a polypeptide encoded by a polynucleotide that hybridizes under low stringency conditions with (i) the mature polypeptide coding sequence of SEQ ID NO: 3, or (ii) the full-length complement of (i);
   c. a polypeptide encoded by a polynucleotide having at least 60% identity to the mature polypeptide coding sequence of SEQ ID NO: 3; and
   d. a fragment of the mature polypeptide of SEQ ID NO: 4, which has asparaginase activity.

49. The variant of Embodiment 48, wherein the parent asparaginase has at least 60%, e.g., at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO: 4.

50. The variant of Embodiment 48 or 49, wherein the parent asparaginase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 3 or (ii) the full-length complement of (i).

51. The variant of any of Embodiments 48-50, wherein the parent asparaginase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 3.

52. The variant of any of Embodiments 48-51, wherein the parent asparaginase comprises or consists of the mature polypeptide of SEQ ID NO: 4.

53. The variant of any of Embodiments 48-52, wherein the parent asparaginase is a fragment of the mature polypeptide of SEQ ID NO: 4, wherein the fragment has asparaginase activity.

54. The variant of any of Embodiments 42-53, which has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent asparaginase.

55. The variant of any of Embodiments 1-54, wherein the variant consists of 325 to 375, e.g., 330 to 370, 335 to 365 or 340 to 360 amino acids.

56. The variant of any of Embodiments 1-55, wherein the number of substitutions is 1-20, e.g., 1-10 or 1-5, such as 1, 2, 3, 4, 5, 6, 7, 8, 9 or 10 substitutions.

57. The variant of any of Embodiments 1-56, which comprises a substitution at two positions corresponding to any of positions 71, 74, 122, 139, 140, 194, 197, 228, 238, 239, 240, 241, 253, 258, 259, 297, 299, 314, 333, 334, 337, 338, 356, 363 or 373.

58. The variant of any of Embodiments 1-56, which comprises a substitution at three positions corresponding to any of positions 71, 74, 122, 139, 140, 194, 197, 228, 238, 239, 240, 241, 253, 258, 259, 297, 299, 314, 333, 334, 337, 338, 356, 363 or 373.

59. The variant of any of Embodiments 1-56, which comprises a substitution at four positions corresponding to any of positions 71, 74, 122, 139, 140, 194, 197, 228, 238, 239, 240, 241, 253, 258, 259, 297, 299, 314, 333, 334, 337, 338, 356, 363 or 373.

60. The variant of any of Embodiments 1-56, which comprises a substitution at five positions corresponding to any of positions 71, 74, 122, 139, 140, 194, 197, 228, 238, 239, 240, 241, 253, 258, 259, 297, 299, 314, 333, 334, 337, 338, 356, 363 or 373.

61. The variant of any of Embodiments 1-56, which comprises a substitution at six positions corresponding to any of positions 71, 74, 122, 139, 140, 194, 197, 228, 238, 239, 240, 241, 253, 258, 259, 297, 299, 314, 333, 334, 337, 338, 356, 363 or 373.

62. The variant of any of Embodiments 1-56, which comprises a substitution at seven positions corresponding to any of positions 71, 74, 122, 139, 140, 194, 197, 228, 238, 239, 240, 241, 253, 258, 259, 297, 299, 314, 333, 334, 337, 338, 356, 363 or 373.

63. The variant of any of Embodiments 1-56, which comprises a substitution at eight positions corresponding to any of positions 71, 74, 122, 139, 140, 194, 197, 228, 238, 239, 240, 241, 253, 258, 259, 297, 299, 314, 333, 334, 337, 338, 356, 363 or 373.

64. The variant of any of Embodiments 1-63, which further comprises a substitution at one or more positions corresponding to positions 70, 307, 323, 327, 349, 351 or 353 of SEQ ID NO: 2.

65. The variant of Embodiment 64, comprising one or more of the following substitutions: N70K, S307A, A323R, T327V, A349Q, S351A or V353I.

66. The variant of any of Embodiments 1-65, which further comprises a substitution at a position corresponding to positions 290.

67. The variant of Embodiment 66 comprising the substitution K290V.

68. A method for producing a food product from a food material, comprising:
  (a) adding the variant of any of Embodiments 1-67 to the food material; and
  (b) heating the enzyme treated food material.

69. The method of Embodiment 68, wherein the variant is added to the food material in an amount that is effective in reducing the level of asparagine present in the food material.

70. The method of Embodiment 68 or 69, wherein the method is for reduction of acrylamide in the food product.

71. The method of any of Embodiments 68-70, wherein the food product is a cereal based product, such as bread, pastry, cake, pretzels, bagels, Dutch honey cake, cookies, gingerbread, gingercake, breakfast cereals or crispbread; a vegetable based product, e.g., a potato based product, such as French fries, sliced potato chips, dough-based potato snacks, fabricated potato products or croquettes; or a coffee based product.

72. The method of any of Embodiments 68-70, wherein the food material is a potato based food material and wherein the food product is a potato based food product.

73. The method of any of Embodiments 68-70, wherein the food material is a coffee based material and wherein the food product is a coffee product.

74. An isolated polynucleotide encoding the variant of any of Embodiments 1-67.

75. A nucleic acid construct comprising the polynucleotide of Embodiment 74.

76. An expression vector comprising the polynucleotide of Embodiment 74.

77. A host cell comprising the polynucleotide of Embodiment 74.

78. A method of producing an asparaginase variant, comprising:
  a. cultivating the host cell of Embodiment 77 under conditions suitable for expression of the variant; and
  b. recovering the variant.

79. A transgenic plant, plant part or plant cell transformed with the polynucleotide of Embodiment 74.

80. A method of producing a variant of any of Embodiments 1-67, comprising:
  a. cultivating a transgenic plant or a plant cell comprising a polynucleotide encoding the variant under conditions conducive for production of the variant; and
  b. recovering the variant.

81. A method for obtaining an asparaginase variant, comprising introducing into a parent asparaginase a substitution at one or more positions corresponding to positions 122, 140, 197, 241, 253 or 373 of the mature polypeptide of SEQ ID NO: 2, wherein the variant has asparaginase activity; and recovering the variant.

82. A method for obtaining an asparaginase variant, comprising introducing into a parent asparaginase, which has at least 80% sequence identity to the mature polypeptide of any of SEQ ID NO: 2 or 4, a substitution at one or more positions corresponding to positions 122, 140, 197, 238, 239, 240, 241, 253, 258, 259, 297 or 373 of SEQ ID NO: 2, wherein the variant has asparaginase activity; and recovering the variant.

83. A method for obtaining an asparaginase variant, comprising introducing into a parent asparaginase one or more of the following substitutions, wherein each position corresponds to a position in SEQ ID NO: 2: T71C, T74C, K122A, K122R, V139G, T140D, K194L, D197E, I228M, S238C, N239C, K240R, P241E, K253R, I258Y, R259C, R259V, S299A, S334W, S338W, G356D, K363R or E373H, wherein the variant has asparaginase activity; and recovering the variant.

84. A method for obtaining an asparaginase variant, comprising introducing into a parent asparaginase, which has at least 80% sequence identity to the mature polypeptide of any of SEQ ID NO: 2 or 4, one or more of the following substitutions, wherein each position corresponds to a position in SEQ ID NO: 2: T71C, T74A, T74C, K122A, K122R, V139G, T140D, K194L, D197E, I228M, S238C, N239C, K240R, P241E, K253R, I258V, I258Y, R259C, R259V, S297V, S299A, T314A, P333L, S334P, S334W, E337S, S338G, S338W, G356D, K363R or E373H, wherein the variant has asparaginase activity; and recovering the variant.

85. The method of any of Embodiments 81-84, where the variant asparaginase has a higher thermostability than the parent asparaginase.

86. The method of any of Embodiments 81-85, where the variant has a higher melting temperature Tm than the parent asparaginase, where the Tm is determined by Differential Scanning calorimetry.

87. A process of producing a fermentation product, comprising:
  (a) liquefying a starch-containing material to a dextrin with an alpha-amylase in the presence of an asparaginase of any of Embodiments 1-67;
  (b) saccharifying the dextrin to a sugar with a saccharifying enzyme; and
  (c) fermenting the sugar using a fermenting organism to produce the fermentation product.

88. A process of producing a fermentation product, comprising:
  (a) treating a starch-containing material with an asparaginase of any of Embodiments 1-67;
  (b) liquefying the treated starch-containing material to a dextrin with an alpha-amylase;
  (c) saccharifying the dextrin to a sugar with a saccharifying enzyme; and
  (d) fermenting the sugar using a fermenting organism to produce the fermentation product.

89. The process of Embodiment 88, wherein the starch-containing material is treated with the asparaginase at a temperature of 20-90° C.

90. The process of Embodiment 89, wherein the asparaginase is an enzyme of EC 3.5.1.1.
91. The process of any of Embodiments 87-90, further comprising recovering the fermentation product.
92. A process of producing a sugar, comprising:
(a) liquefying a starch-containing material to a dextrin with an alpha-amylase in the presence of an asparaginase of any of Embodiments 1-67; and
(b) saccharifying the dextrin to a sugar with a saccharifying enzyme.
93. The process of Embodiment 92, wherein the sugar is maltose.
94. The process of Embodiment 92, wherein the sugar is glucose.
95. The process of Embodiment 94, further comprising converting glucose to fructose.
96. The process of any of Embodiments 92-95, wherein the starch-containing material is liquefied to the dextrin in the presence of the asparaginase.
97. The process of Embodiment 92, wherein the asparaginase is an enzyme of EC 3.5.1.1.
98. A process of producing a sugar, comprising:
(a) treating a starch-containing material with an asparaginase of any of Embodiments 1-67;
(b) liquefying the treated starch-containing material to a dextrin with an alpha-amylase; and
(c) saccharifying the dextrin to a sugar with a saccharifying enzyme.
99. The process of Embodiment 98, wherein the sugar is maltose.
100. The process of Embodiment 98, wherein the sugar is glucose.
101. The process of Embodiment 100, further comprising converting glucose to fructose.
102. The process of any of Embodiments 92-101, wherein the starch-containing material is treated with the asparaginase at a temperature of 20-90° C.
103. The process of Embodiment 98, wherein the asparaginase is an enzyme of EC 3.5.1.1.
104. The process of any of Embodiments 98-103, further comprising recovering the sugar.
105. The process of any of Embodiments 95-97 and 101-104, further comprising recovering the fructose.
106. A process of producing a dextrin, comprising
(a) liquefying a starch-containing material to the dextrin with an alpha-amylase in the presence of an asparaginase of any of Embodiments 1-67.
107. The process of Embodiment 106, wherein the starch-containing material is liquefied to the dextrin in the presence of the asparaginase.
108. The process of Embodiment 106, wherein the asparaginase is an enzyme of EC 3.5.1.1.
109. A process of producing a dextrin, comprising:
(a) treating a starch-containing material with an asparaginase of any of Embodiments 1-67; and
(b) liquefying the treated starch-containing material to a dextrin with an alpha-amylase.
110. The process of Embodiment 109, wherein the starch-containing material is treated with the asparaginase at a temperature of 20-90° C.
111. The process of Embodiment 109, wherein the asparaginase is an enzyme of EC 3.5.1.1.
112. The process of any of Embodiments 106-111, further comprising recovering the dextrin.
113. The process of any of Embodiments 87-112, wherein the starch-containing material is liquefied to a dextrin at a temperature of 65-110° C., e.g., 80-100° C. or 80-90° C.
114. The process of any of Embodiments 87-113, wherein the liquefaction comprises jet-cooking at a temperature between 95-140° C.
115. The process of any of Embodiments 87-114, further comprising pre-saccharification of typically 40-90 minutes at a temperature between 20-75° C., preferably 25-65° C.
116. The process of any of Embodiments 87-115, wherein the saccharification is carried out at a temperature in the range of 20-75° C., preferably 25-65° C.
117. The process of any of Embodiments 87-116, wherein the saccharifying enzyme is a beta-amylase, glucoamylase, or maltogenic alpha-amylase.
118. The process of any of Embodiments 87-117, wherein the dextrin is saccharified to the sugar with a saccharifying enzyme and a pullulanase and/or isoamylase.
119. The process of any of Embodiments 87-118, wherein the saccharification and/or the fermentation are carried out in the presence of a protease.
120. The process of any of Embodiments 87-119, wherein the saccharification and fermentation are performed simultaneously.
121. The process of Embodiment 120, wherein the saccharification and fermentation are carried out at a temperature of 20-40° C.
122. The process of any of Embodiments 87-121, wherein the starch-containing material is selected from the group consisting of barley, beans, cassava, cereals, corn, milo, peas, potatoes, rice, rye, sago, sorghum, sweet potatoes, tapioca, wheat, and whole grains, or any mixture thereof.
123. A process of producing a fermentation product, comprising converting a starch-containing material to a dextrin with an alpha-amylase; saccharifying the dextrin to a sugar with a glucoamylase; and fermenting the sugar using a fermenting organism in the presence of an an asparaginase of any of Embodiments 1-67 in a single step at a temperature below the initial gelatinization temperature of the starch-containing material.
124. The process of any of Embodiments 87-123, wherein the fermentation product is selected from the group consisting of alcohols (e.g., butanol, ethanol, methanol, 1,3-propanediol); organic acids (e.g., acetic acid, citric acid, itaconic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones.
125. The process of Embodiment 124, wherein the fermentation product is ethanol.
126. The process of any of Embodiments 87-125, wherein the fermenting organism is a yeast.
127. A process of producing a fermentation product, comprising
(a) treating a plant extract containing amino acid(s) and soluble sugar(s) with an asparaginase of any if Embodiments 1-67;
(b) producing molasses from the treated plant extract;
(c) diluting the molasses; and
(d) fermenting the diluted molasses with a fermenting organism to produce the fermentation product.
128. The process of Embodiment 127, wherein the plant extract is treated with an asparaginase.
129. The process of Embodiment 127, wherein the asparaginase is an enzyme of EC 3.5.1.1.
130. The process of any of Embodiments 127-129, wherein the plant extract is raw sugarcane juice or clarified sugarcane juice.

131. The process of any of Embodiments 127-130, wherein the production of molasses comprises
   (x) clarification of the plant extract;
   (y) concentration of sugars found in the clarified plant extract (e.g., by evaporation) to form a syrup; and
   (z) crystallization of sucrose from the syrup to form the molasses.
132. The process of any of Embodiments 127-131, wherein step (a) occurs at any time prior to evaporation.
133. The process of Embodiment 132, wherein step (a) occurs during juice extraction, crushing, juice recovery, and/or juice clarification.
134. A process of producing a fermentation product, comprising:
   (a) treating a plant extract containing amino acid(s) and soluble sugar(s) with an asparaginase of any of Embodiments 1-67; and
   (b) fermenting the treated plant extract with a fermenting organism to produce the fermentation product.
135. The process of Embodiment 134, wherein the plant extract is treated with the asparaginase.
136. The process of Embodiment 134, wherein the asparaginase is an enzyme of EC 3.5.1.1.
137. The process of any of Embodiments 127-136, wherein the plant extract is raw sugarcane juice or clarified sugarcane juice.
138. The process of any of Embodiments 127-137, further comprising recovering the fermentation product.
139. The process of any of Embodiments 127-138, wherein the fermentation product is selected from the group consisting of alcohols (e.g., butanol, ethanol, methanol, 1,3-propanediol); organic acids (e.g., acetic acid, citric acid, itaconic acid, gluconic acid, gluconate, lactic acid, succinic acid, 2,5-diketo-D-gluconic acid); ketones (e.g., acetone); amino acids (e.g., glutamic acid); gases (e.g., H2 and CO2), and more complex compounds, including, for example, antibiotics (e.g., penicillin and tetracycline); enzymes; vitamins (e.g., riboflavin, B12, beta-carotene); and hormones.
140. The process of Embodiment 139, wherein the fermentation product is ethanol.
141. The process of any of Embodiments 127-140, wherein the fermenting organism is a yeast.
142. A process of producing a sugar, comprising:
   (a) treating a plant extract containing amino acid(s) and soluble sugar(s) with an asparaginase of any of Embodiments 1-67; and
   (b) recovering the sugar from the plant extract.
143. The process of Embodiment 142, wherein the sugar is fructose, galactose, glucose, maltose, or sucrose.
144. A process of producing sucrose, comprising:
   (a) treating a plant extract containing amino acid(s) and soluble sugar(s) with an an asparaginase;
   (b) clarification of the plant extract;
   (c) concentration of sugars found in the clarified plant extract (e.g., by evaporation) to form a syrup containing sucrose;
   (d) crystallization of sucrose from the syrup; and
   (e) recovering sucrose.
145. The process of Embodiment 144, wherein the plant extract is treated with the asparaginase.
146. The process of Embodiment 144, wherein the asparaginase is an enzyme of EC 3.5.1.1.
147. The process of any of Embodiments 144-146, wherein the plant extract is raw sugarcane juice or clarified sugarcane juice.
148. The process of any of Embodiments 144-147, wherein step (a) occurs at any time prior to evaporation.
149. The process of Embodiment 148, wherein step (a) occurs during juice extraction, crushing, juice recovery, and/or juice clarification.
150. The process of any of Embodiments 144-149, wherein raw sugarcane juice is treated with the asparaginase.
151. The process of any of Embodiments 144-150, wherein sugarcane juice clarified for sugar production is treated with the asparaginase.
152. The process of any of Embodiments 144-151, wherein sugarcane juice clarified for ethanol production is treated with the asparaginase.
153. The process of any of Embodiments 144-152, wherein the plant extract is selected from the group consisting of sweet sorghum, sugar beets, sugar cane, or any mixture thereof.
154. The process of any of Embodiments 144-153, wherein the raw juice is clarified for sugar and/or ethanol production at a pH of 7.5-9, e.g., 8-9.

The present invention is further described by the following examples that should not be construed as limiting the scope of the invention.

EXAMPLES

Example 1

Asparaginase Activity (ASNU) Assay

The activity of asparaginase may be measured in ASNU. An asparaginase unit (ASNU) is defined as the amount of enzyme needed to generate 1.0 micromole of ammonia in 1 minute at 37° C. and pH 7.0, in 0.1 M MOPS buffer with 9.2 mg/ml asparagine.

Asparaginase hydrolyzes asparagine to aspartic acid and ammonium. The produced ammonium is combined with α-ketoglutarate to form glutamic acid whereby NADH is oxidized to NAD+. The reaction is catalysed by a surplus of glutamate dehydrogenase. The consumption of NADH is measured by photometry at 340 nm. NADH has an absorbance at 340, while NAD+ has no absorbance. A decrease in color is thus measured, and can be correlated to asparaginase activity.

Activity is determined relative to an asparaginase standard of known activity. A commercial product having a declared activity like Acrylaway L may be used as standard.

Glucoamylase Activity (AGU)

Glucoamylase activity may be measured in Glucoamylase Units (AGU). The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1 M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Alpha-Amylase Activity (KNU)

Alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

Acid Alpha-Amylase Activity (AFAU)

The activity of an acid alpha-amylase may be measured in AFAU (Acid Fungal Alpha-amylase Units) or FAU-F. Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, EC 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions as provided in the FIGURE.

| Standard conditions/reaction conditions: | |
|---|---|
| Substrate: | Soluble starch, approx. 0.17 g/L |
| Buffer: | Citrate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

Protease Assay Method—AU(RH)

Proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e., 25° C., pH 5.5 and 10 minutes reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assay Method (LAPU)

One Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Maltogenic Amylase Activity (MANU)

One MANU (Maltogenic Amylase Novo Unit) is the amount of enzyme required to release one micromole of maltose per minute at a concentration of 10 mg of maltotriose (Sigma M 8378) substrate per ml of 0.1 M citrate buffer, pH 5.0 at 37° C. for 30 minutes.

Example 2: Construction of Yeast Libraries and Site-Directed Variants

Materials and Methods:

Strains and Plasmids

E. coli DH12S (available from Gibco BRL) was used to rescue plasmids from yeast.

pJN065N2 is an S. cerevisiae and E. coli shuttle vector under the control of TPI promoter, derived from pJN001N2 described in WO 2008/110513, in which the mature part of Aspergillus oryzae asparaginase protein engineered gene has been inserted. pJN001N2 has the signal sequence from Humicola insolens cutinase (MKFFTTILSTASLVAALP) followed by the sequence of the mature part of Aspergillus oryzae asparaginase (amino acids 27-378 of SEQ ID NO: 2). pJN065N2 encodes the JN065 variant having the amino acid substitutions N70K A323R T327V A349Q S351A V353I as compared to the wild type Aspergillus oryzae asparaginase. In WO 2008/110513, the JN065 variant was referred to as JN065N2.

Saccharomyces cerevisiae YNG318: MATa Dpep4[cir+] ura3-52, leu2-D2, his 4-539 was used for asparaginase variants expression. It is described in J. Biol. Chem. 272 (15): 9720-9727 (1997).

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/l, 5% threonine 4 ml/l, 1% tryptophan 10 ml/l, 20% casamino acids 25 ml/l, 10× basal solution 100 ml/l. The solution is sterilized using a filter of a pore size of 0.20 micrometer. Agar and $H_2O$ (approx. 761 ml) is autoclaved together, and the separately sterilized SC-glucose solution added to the agar solution.

YPD: Bacto peptone 20 g/l, yeast extract 10 g/l, 20% glucose 100 ml/l.

PEG/LiAc solution: 40% PEG4000 50 ml, 5 M Lithium Acetate 1 ml

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (eds.).

Yeast Transformation

Yeast transformation was carried out by lithium acetate method: 0.5 microL of vector digested by appropriate restriction endnucleases, 1 microL of PCR fragments and 10 microL of carrier DNA (Clontech) were mixed and added to 100 microL of YNG318 competent cells on ice. 0.6 ml PEG/LiAc solution was added to the cells and mixed gently. The mixture was incubated for 30 min at 30° C., 200 rpm and then heated to 42° C. for 15 min.

The suspension was centrifuged for 5 sec. and precipitated yeast cells were resolved in 1 ml of YPD and poured onto SC-glucose plates. The plates were incubated at 30° C. for 3 days to make colonies. Yeast total DNA was extracted by the Robzyk and Kassir's method described in *Nucleic Acids Research* 20(14): 3790 (1992).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Libraries in yeast and site-directed variants were constructed by SOE PCR method (Splicing by Overlap Extension, see "PCR: A practical approach", p. 207-209, Oxford University press, eds. McPherson, Quirke, Taylor), followed by introduction of the purified PCR fragments mixed with vector digest into *Saccharomyces cerevisiae* for in vivo recombination.

General Primers for Amplification and Sequencing

The below primers are used to make DNA fragments containing any mutated fragments by the SOE method together with degenerated primers (AM34+Reverse primer and AM35+forward primer) or just to amplify a whole asparaginase gene (AM34+AM35).

AM34
TAGGAGTTTAGTGAACTTGC

AM35
TTCGAGCGTCCCAAAACC

| PCR reaction system: | Conditions: |
|---|---|
| 48.5 micro L H2O | 1 94° C. 2 min |
| PureTaq Ready To Go | 2 94° C. 30 sec |
| 0.5 micro L × 2 100 pmole/micro L | 3 55° C. 30 sec |
| Primers | 4 72° C. 90 sec |
| 0.5 micro L Template DNA | 2-4 25 cycles |
| | 5 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Example 3: Library Screening

Yeast clones/libraries were prepared as in Example 2, using JN065 or JN070 variants as a template. Clones on SC-glucose were inoculated in a well of a 96-well micro titre plate containing YPD medium and cultivated at 28° C. for 3 days. To determine the remaining activity after heat treatment, the asparagine hydrolyzing activity of the culture supernatant was measured at 55° C. after incubating for 20 minutes at elevated temperature (4° C. as a reference). Then the clones with increased remaining activity were selected and the sequences were confirmed.

Asparaqinase Activity Assay (rASNU Assay)—Used in Examples 3, 8, 9, 10, 11 and 12

Reagents:

1 M Potassium phosphate buffer (pH 6.0)

1 M $KH_2PO_4$ (136 g/500 ml)+1 M $K_2HPO_4$ (174 g/500 ml)

Adjust to pH 6.0

100 mM Potassium phosphate buffer (pH 6.0)+0.1% tritonX-100 (1 L)

100 ml 1 M Potassium phosphate buffer (pH 6.0)

1 g Triton X-100

Adjust to 1000 ml

2 M Hydroxylamine (HA) solution (100 ml)

13.9 g hydroxylamine

Adjust to 100 ml with 100 mM potassium phosphate buffer (pH 6)

Stop solution (500 ml)

23.83 ml acetate 13.88 g $FeCl_3$ $6H_2O$ 84 ml 5 N HCl

Adjust to 500 ml with $H_2O$

Substrate solution (100 ml)

10 ml 1 M Potassium phosphate buffer 0.5 g L-asparagine 5 ml 2 M HA soln.

Adjust to 100 ml with $H_2O$

Activity Assay:

1 Pipette 20 microL sample into a well.

2 Add 100 microL of substrate solution into the well.

3 Incubate 20 min. at 55° C. (or as otherwise indicated)

4 Add 100 microL of stop solution into the well.

5 Measure A490.

Compare result to that of a control for a relative effect or to a standard of known activity in ASNU. Activity as determined according to this assay is referred to as rASNU.

Thermostability Screening:

For initial screening of the variants for improved thermostability, the 96 sample well plate is incubated at relevant screening temperature for 20 min (4° C. for a control). Substrate solution is then added and the plate incubated for 20 min. at 55° C. and handled as above.

Variants Tested:

Clone JN065 holds the amino acid substitutions at N70K A323R T327V A349Q S351A V353I over the wild type Aspergillus oryzae asparaginase described in WO 2008/110513 (see SEQ ID NO: 6).

A27* means the amino acid A27 is deleted.

TABLE 1

| Substitutions to the WT | |
|---|---|
| Variant | Substitutions |
| JN070 | N70K S307A A323R T327V A349Q S351A V353I |
| JN077 | N70K V128C A323R T327V A349Q S351A V353I |
| JN095 | N70K A323R T327V A349Q S351A V353I K363R |

TABLE 2

| Substitutions to JN070 | |
|---|---|
| JN079 | A27* T28* D29* |
| JN096 | K194L |
| JN097 | S283C |
| JN101 | K122R |
| JN102 | K122A |
| JN109 | K122A K194L S283C |
| JN110 | K122R K194L S283C |
| JN111 | K122A K194L |
| JN113 | K194L S283C |
| JN115 | K249L |
| JN116 | K290V |
| JN117 | K290V |
| JN120 | K70R |
| JN124 | K194L |
| JN126 | E337S |
| JN135 | S297V S299A |
| JN140 | S334P |
| JN141 | K240R E373H |
| JN145 | S338W |
| JN147 | K70R S338W |
| JN148 | K290V S338W |
| JN149 | K70N K290V |
| JN150 | K70N |
| JN152 | S299A |
| JN153 | S334W |

TABLE 2-continued

| Substitutions to JN070 | |
|---|---|
| JN155 | P241E |
| JN158 | K122A P241E S299A |
| JN159 | K122A K290V S338W |
| JN161 | K122A P241E K290V S299A S338W |
| JN162 | K122A P241E K290V S338W |
| JN164 | K122A S299A S334P |
| JN165 | K122A S299A S334P |
| JN166 | K122A P241E S334P |
| JN167 | K122A P241E S299A S334P |
| JN168 | K122A K290V S334P S338W |
| JN176 | T74C S238C |
| JN177 | T71C N239C |
| JN178 | K122A K240R P241E S299A S334P |
| JN179 | K122A K240R P241E K253R S299A S334P |
| JN180 | K122A K240R P241E S299A S334P E337S |
| JN181 | K122A K240R P241E K253R S299A S334P E337S |
| JN182 | K122A P241E S299A S334P E337S |
| JN183 | K122A P241E S299A S334P S338W |
| JN184 | K122A P241E S299A S334W |
| JN185 | K122A P241E S299A S334W S338W |
| JN191 | T74A |
| JN193 | K122R V139G T140D I258Y |
| JN195 | K122A P241E R259C |
| JN196 | K122A R259V |
| JN197 | K122A P241E S299A S307D S338G |
| JN226 | A27* T28* D29* K122A P241E S299A S334P S338W |
| JN262 | I228M T314A P333L G356D |
| JN265 | D197E S215T I258V |

Results:

TABLE 3

| Residual activity after 70° C. incubation | |
|---|---|
| Variant | |
| JN070 | 86% (JN065 81%) |
| JN077 | 49% (JN065 38%) |
| JN095 | 76% (JN065 46%) |

TABLE 4

Residual activity after incubation at elevated temperatures

| | Residual activity after 20 min-incubation at | | | |
|---|---|---|---|---|
| | 70° C. | 73° C. | 76° C. | 78° C. |
| JN079 | 91%(JN070 52%) | 49%(JN070 24%) | 18% (JN070 6%) | |
| JN096 | 79%(JN070 70%) | 36%(JN070 10%) | 6%(JN070 4%) | |
| JN097 | 81%(JN070 70%) | 31%(JN070 10%) | 7%(JN070 4%) | |
| JN101 | 91%(JN070 87%) | 81%(JN070 76%) | | |
| JN102 | 87%(JN070 87%) | 87%(JN070 76%) | | |
| JN109 | 79%(JN070 76%) | 63%(JN070 28%) | 10%(JN070 1%) | |
| JN110 | 80%(JN070 76%) | 61%(JN070 28%) | 7%(JN070 1%) | |
| JN111 | 76%(JN070 76%) | 58%(JN070 28%) | 2%(JN070 1%) | |
| JN113 | 77%(JN070 76%) | 55%(JN070 28%) | 2%(JN070 1%) | |
| JN115 | 83%(JN070 80%) | 67%(JN070 59%) | 11%(JN070 1%) | |
| JN116 | 83%(JN070 80%) | 69%(JN070 59%) | 12%(JN070 1%) | |
| JN117 | 86%(JN070 80%) | 75%(JN070 59%) | 21%(JN070 1%) | |
| JN120 | 80%(JN070 80%) | 66%(JN07059%) | 9%(JN070 1%) | |
| JN124 | 86%(JN070 80%) | 70%(JN070 59%) | 9%(JN070 1%) | |
| JN126 | 88%(JN070 73%) | 50%(JN070 14%) | 2%(JN070 1%) | |
| JN135 | 75%(JN070 73%) | 67%(JN070 14%) | 36%(JN070 1%) | |
| JN140 | 82%(JN070 79%) | 61%(JN070 37%) | 57%(JN070 32%) | |
| JN141 | 82%(JN070 79%) | 53%(JN070 37%) | 32%(JN070 32%) | |
| JN145 | 79%(JN070 70%) | 72%(JN070 35%) | 53%(JN070 1%) | |
| JN147 | 98%(JN070 85%) | 89%(JN070 60%) | 89%(JN070 30%) | |
| JN148 | 79%(JN070 54%) | 74%(JN070 22%) | 55%(JN070 21%) | |
| JN149 | 89%(JN070 85%) | 67%(JN070 60%) | 28%(JN070 30%) | |
| JN150 | 80%(JN070 85%) | 52%(JN070 60%) | 23%(JN070 30%) | |

TABLE 4-continued

Residual activity after incubation at elevated temperatures

| | Residual activity after 20 min-incubation at | | | |
|---|---|---|---|---|
| | 70° C. | 73° C. | 76° C. | 78° C. |
| JN152 | 106%(JN070 95%) | 105%(JN070 58%) | 99%(JN070 47%) | |
| JN153 | 89%(JN070 70%) | 70%(JN070 18%) | 21%(JN070 15%) | |
| JN155 | 94%(JN070 81%) | 84%(JN070 39%) | 55%(JN070 1%) | |
| JN158 | 100%(JN070 85%) | 94%(JN070 60%) | 88%(JN070 30%) | |
| JN159 | 98%(JN070 85%) | 88%(JN070 60%) | 82%(JN070 30%) | |
| JN161 | 101%(JN070 85%) | 97%(JN070 60%) | 90%(JN070 30%) | |
| JN162 | 103%(JN070 85%) | 97%(JN070 60%) | 86%(JN070 30%) | |
| JN164 | 98%(JN070 85%) | 88%(JN070 60%) | 78%(JN070 30%) | |
| JN165 | 99%(JN070 85%) | 92%(JN070 60%) | 87%(JN070 30%) | |
| JN166 | 104%(JN070 85%) | 92%(JN070 60%) | 87%(JN070 30%) | |
| JN167 | 110%(JN070 85%) | 104%(JN070 60%) | 99%(JN070 30%) | |
| JN168 | 96%(JN070 85%) | 80%(JN070 60%) | 59%(JN070 30%) | |
| JN176 | 97%(JN070 79%) | 92%(JN070 56%) | 91%(JN070 34%) | |
| JN177 | 93%(JN070 79%) | 92%(JN070 56%) | 71%(JN070 34%) | |
| JN178 | 94%(JN070 71%) | 92%(JN070 13%) | 89%(JN070 6%) | 86%(JN070 5%) |
| JN179 | 92%(JN070 71%) | 92%(JN070 13%) | 83%(JN070 6%) | 84%(JN070 5%) |
| JN180 | 96%(JN070 71%) | 94%(JN070 13%) | 85%(JN070 6%) | 85%(JN070 5%) |
| JN182 | 95%(JN070 71%) | 92%(JN070 13%) | 85%(JN070 6%) | 87%(JN070 5%) |
| JN183 | 101%(JN070 71%) | 95%(JN070 13%) | 91%(JN070 6%) | 88%(JN070 5%) |
| JN185 | 86% (JN070 44%) | 84% (JN070 3%) | 72%(JN070 2%) | 74% (JN070 2%) |
| JN191 | 80% (JN070 62%) | 70% (JN070 12%) | 53%(JN070 2%) | |
| JN193 | 84% (JN070 62%) | 62%(JN070 12%) | 2%(JN070 2%) | |
| JN195 | 91%(JN070 62%) | 82%(JN070 12%) | 38%(JN070 2%) | |
| JN196 | 77%(JN070 62%) | 55%(JN070 12%) | 4%(JN070 2%) | |
| JN197 | 93%(JN070 62%) | 90%(JN070 12%) | 82% (JN070 2%) | |
| JN262 | 57% (JN070 49%) | 57% (JN070 49%) | | |
| JN265 | 63% (JN070 49%) | 63% (JN070 49%) | | |

Example 4: Expression of Asparaginase Variants in *Aspergillus*

The constructs comprising the asparaginase variant genes in example above were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). The *Aspergillus* selective marker amdS from *Aspergillus nidulans* enabling growth on acetamide as sole nitrogen source was also present on the plasmid. The expression plasmids for asparaginase variants were transformed into *Aspergillus* as described in Lassen et al., 2001, *Applied and Environmental Micorbiology* 67: 4701-4707. For each of the constructs 10-20 strains were isolated, purified and cultivated in shake flasks.

Example 5: Purification of Asparaginase Variants

Purification of asparaginase variants was carried out by three steps: batch purification using Hydrophobic Interaction Chromatography (HIC) media, HIC column and Anion Exchange Chromatography column. Finally, the samples were dialyzed against 10 L of 20 mM sodium acetate buffer pH 5.5 using 12 k-14 k MWCO dialysis membrane.

Example 6: Enzyme Thermostability Measurement (TSA)

Purified enzyme was diluted with 0.5% SAPP pH 5.0 to 0.5 mg/ml and mixed with the equal volume of SYPRO Orange (Invitrogen) diluted with Milli-Q water. Thirty microliters of mixture solution was transfer to LightCycler 480 Multiwell Plate 96 (Roche Diagnostics) and the plate was sealed.

Equipment parameters of TSA:
Apparatus: LightCycler 480 Real-Time PCR System (Roche Applied Science)
Scan rate: 0.02° C./sec
Scan range: 37-96° C.
Integration time: 1.0 sec
Excitation wave length 465 nm
Emission wave length 580 nm The obtained fluorescence signal was normalized into a range of 0 and 1. The Melting temperature (Tm) was defined as the temperature where the normalized value is closest to 0.5.

TABLE 5

Tm by TSA assay

| Variant No. | Tm by TSA (° C.) |
|---|---|
| WT | 64.5-64.7 |
| JN065 | 70.43 |
| JN070 | 72.2-72.9 |
| JN079 | 72.77 |
| JN102 | 73.49 |
| JN117 | 73.54 |
| JN135 | 77.19 |
| JN140 | 75.53 |
| JN145 | 77 |
| JN148 | 76.91 |
| JN152 | 76.69 |
| JN158 | 77.8 |
| JN159 | 76.76 |
| JN161 | 81.83 |
| JN162 | 79.15 |
| JN165 | 80.05 |
| JN166 | 79.71 |
| JN167 | 80.87 |
| JN168 | 80.32 |
| JN178 | 81.91 |
| JN179 | 80.04 |
| JN180 | 83.72 |

TABLE 5-continued

| Tm by TSA assay | |
|---|---|
| Variant No. | Tm by TSA (° C.) |
| JN181 | 81.91 |
| JN182 | 83.03 |
| JN183 | 82.17 |
| JN184 | 77.53 |
| JN226 | 87.93 |

Example 7: Enzyme Thermostability Measurement (DSC)

Sample Preparation for Differential Scanning Calorimetry (DSC):
  Sample was transferred to a Slide-A-Lyzer® Dialysis Cassette (Pierce, cat. #66380, 10 kDa MWCO) and dialyzed against 20 mM sodium acetate, pH 5.0.
  The dialysis buffer was used for blanking in concentration determination by absorption measurement at 280 nm (A280) and as a reference for DSC.
  The volume of the sample was adjusted using the dialysis buffer until an A280 of approx. 0.5-0.55 was obtained. Employing an extinction coefficient calculated based on amino acid sequence data (Vector NTI v. 9.0.0), this corresponds to an enzyme concentration of approx. 1.5-1.7 mg/ml.
  The samples were degassed by vacuum suction and magnetic stirring for approx. 10 minutes prior to loading into the DSC apparatus.
DSC Data Recording and Processing:
  Apparatus: VP-Capillary DSC, MicroCal (GE Healthcare)
  Scan interval: 20-110° C.
  Scanrate: 200° C./h
  Data processing software: OriginLab MicroCal LLC Cap DSC
The thermal denaturation temperature (Td) was determined as the temperature corresponding to the apex of the signal in the thermogram.

TABLE 6

| Td by DSC assay | |
|---|---|
| Sample | Td |
| JN065 | 75.5 |
| JN102 | 77.9 |
| JN117 | 77.7 |
| JN140 | 81.2 |
| JN145 | 80.3 |
| JN152 | 80.9 |
| JN158 | 83.2 |
| JN162 | 83.1 |
| JN180 | 88.2 |
| JN183 | 88.6 |

Example 8: Enzyme Thermostability in 0.5% SAPP

Purified enzyme was diluted with 0.5% sodium dihydrogen pyrophosphate (SAPP) pH 5.0 to a concentration around 6 rASNU/ml. Fifty microliters of diluted enzyme solution was transferred to a 96-well PCR plate and incubated at 70-80° C. for 4 hours by using a thermal cycler. Immediately after incubation, 10 microL of incubated solution was added to 100 microL of pre-incubated substrate solution of rASNU assay in a 96-well plate and incubated at 37 or 50° C. for 20 min. The reaction was stopped by adding 100 microL of stop solution and the absorbance at 490 nm was measured. The residual activity was determined using the activity of a similar sample incubated at 25° C. as a control.

TABLE 7

| Residual activity after 4 hours | | | | | | |
|---|---|---|---|---|---|---|
| | residual after 4 h in 0.5% SAPP, pH 5 | | | | | |
| Variant No. | 70° C. | 72° C. | 74° C. | 76° C. | 78° C. | 80° C. |
| WT | 1% | 1% | | | | |
| JN065 | 1% | 2% | | | | |
| JN070 | 35% | 1% | 2% | 1% | 1% | |
| JN079 | 30% | 3% | | | | |
| JN102 | 53% | 6% | 2% | 2% | 1% | |
| JN117 | 61% | 6% | 1% | 1% | 1% | |
| JN135 | 88% | 72% | 21% | 1% | 1% | |
| JN140 | 67% | 52% | 21% | 2% | 1% | |
| JN145 | 90% | 71% | 17% | 2% | 1% | |
| JN148 | 74% | 62% | 26% | 2% | 1% | |
| JN152 | 79% | 67% | 25% | 0% | 0% | |
| JN158 | 93% | 79% | 67% | 43% | 2% | |
| JN159 | 86% | 75% | 47% | 3% | 0% | |
| JN161 | 100% | 99% | 95% | 77% | 71% | |
| JN162 | 102% | 97% | 91% | 50% | 1% | |
| JN165 | 98% | 92% | 80% | 64% | 37% | |
| JN166 | 100% | 95% | 85% | 61% | 9% | |
| JN167 | 103% | 101% | 97% | 82% | 68% | |
| JN168 | 104% | 97% | 87% | 72% | 25% | |
| JN178 | 103% | 103% | 99% | 92% | 78% | 33% |
| JN179 | 93% | 87% | 81% | 74% | 53% | 10% |
| JN180 | 100% | 106% | 104% | 96% | 83% | 64% |
| JN181 | 100% | 100% | 96% | 87% | 72% | 35% |
| JN182 | 101% | 102% | 99% | 94% | 76% | 59% |
| JN183 | 99% | 100% | 98% | 94% | 76% | 62% |
| JN184 | 94% | 87% | 64% | 48% | 22% | 0% |
| JN226 | 100% | 103% | 102% | 96% | 90% | 76% |

Example 9: Temperature Activity

Purified enzyme was diluted with 20 mM sodium acetate buffer pH 5.5 to a concentration around 2 rASNU/ml. Ten microliters of enzyme solution was added to 100 microL of substrate solution pre-incubated at different temperature in a 96-well PCR plate and incubated for 20 min. The reaction was stopped by adding 100 microL of stop solution and the absorbance at 490 nm was measured.

TABLE 8

| Temperature activity in percentage of activity at 50° C. | | | |
|---|---|---|---|
| Variant | Thermoactivity (100% @ 50° C.) | | |
| No. | 35° C. | 60° C. | 70° C. |
| WT | 78% | 64% | 4% |
| JN065 | 67% | 68% | 24% |
| JN070 | 64% | 68% | 25% |
| JN079 | 66% | 68% | 26% |
| JN102 | 69% | 73% | 26% |
| JN117 | 63% | 69% | 30% |
| JN135 | 79% | 72% | 29% |
| JN140 | 69% | 67% | 34% |
| JN145 | 72% | 68% | 25% |
| JN148 | 67% | 75% | 29% |
| JN152 | 57% | 79% | 35% |
| JN158 | 51% | 79% | 38% |
| JN159 | 67% | 68% | 27% |
| JN161 | 51% | 82% | 39% |
| JN162 | 63% | 73% | 31% |
| JN165 | 55% | 77% | 38% |

TABLE 8-continued

Temperature activity in percentage of activity at 50° C.

| Variant No. | Thermoactivity (100% @ 50° C.) | | |
|---|---|---|---|
| | 35° C. | 60° C. | 70° C. |
| JN166 | 63% | 69% | 30% |
| JN167 | 53% | 83% | 42% |
| JN168 | 71% | 71% | 31% |
| JN178 | 50% | 83% | 42% |
| JN179 | 45% | 83% | 41% |
| JN180 | 39% | 92% | 51% |
| JN181 | 38% | 96% | 52% |
| JN182 | 41% | 92% | 50% |
| JN183 | 57% | 77% | 37% |
| JN184 | 58% | 92% | 46% |
| JN226 | 59% | 84% | 41% |

Example 10: pH Stability at 70° C.

Purified enzyme was diluted with 0.5% SAPP pH 4.0-7.0 (pH was adjusted using HCl or NaOH) to a concentration around 6 rASNU/ml. Fifty microliters of diluted enzyme solution was transferred to a 96-well PCR plate and incubated at 70° C. for 2 hours. Immediately after incubation, 10 microL of incubated solution was added to 100 microL of preincubated substrate solution of rASNU assay in a 96-well plate and incubated at 50° C. for 20 min. The reaction was stopped by adding 100 microL of stop solution and the absorbance at 490 nm was measured. The residual activity was determined using the activity of a similar sample incubated at 25° C. as a control.

TABLE 9 pH stability

| Variant No. | pH stability @70° C., 2 h | | | |
|---|---|---|---|---|
| | pH 4 | pH 5 | pH 6 | pH 7 |
| WT | 0% | 0% | 0% | 0% |
| JN065 | 10% | 12% | 0% | 0% |
| JN070 | 68% | 55% | 0% | 0% |
| JN079 | 53% | 57% | 0% | 0% |
| JN102 | 62% | 64% | 0% | 0% |
| JN117 | 77% | 78% | 0% | 0% |
| JN135 | 93% | 94% | 10% | 0% |
| JN140 | 74% | 77% | 28% | 0% |
| JN145 | 93% | 99% | 46% | 0% |
| JN148 | 77% | 80% | 44% | 0% |
| JN152 | 91% | 92% | 27% | 0% |
| JN158 | 93% | 98% | 73% | 0% |
| JN159 | 87% | 91% | 69% | 0% |
| JN161 | 98% | 100% | 94% | 74% |
| JN162 | 98% | 102% | 93% | 1% |
| JN165 | 98% | 100% | 84% | 2% |
| JN166 | 95% | 98% | 81% | 0% |
| JN167 | 105% | 103% | 92% | 40% |
| JN168 | 108% | 105% | 95% | 12% |
| JN178 | 105% | 106% | 99% | 37% |
| JN179 | 109% | 104% | 94% | 4% |
| JN180 | 109% | 116% | 102% | 74% |
| JN181 | 110% | 112% | 100% | 38% |
| JN182 | 109% | 112% | 101% | 74% |
| JN183 | 106% | 104% | 98% | 75% |
| JN184 | 94% | 84% | 54% | 0% |
| JN226 | 99% | 99% | 92% | 80% |

Example 11: pH Activity

Purified enzymes were diluted with 20 mM sodium acetate buffer pH 5.5 to a concentration around 2 rASNU/ml. Ten microliters of enzyme solution was added to 100 microL of preincubated substrate solution with different pH constructed by mixing 2-fold substrate solution of rASNU assay and equal volume of 200 mM Britton-Robinson buffer (pH 2.5-11.5). After 20 min incubation at 50° C., the reaction was stopped by adding 100 microL of stop solution and the absorbance at 490 nm was measured.

TABLE 10 pH activity

| Variant No. | pH activity pH 5/pH 6.5 @ 50° C. |
|---|---|
| WT | 36% |
| JN065 | 41% |
| JN070 | 44% |
| JN079 | 42% |
| JN102 | 45% |
| JN117 | 47% |
| JN140 | 50% |
| JN145 | 43% |
| JN148 | 44% |
| JN152 | 52% |
| JN158 | 53% |
| JN159 | 45% |
| JN161 | 55% |
| JN162 | 45% |
| JN165 | 61% |
| JN166 | 51% |
| JN167 | 59% |
| JN168 | 53% |
| JN178 | 59% |
| JN179 | 57% |
| JN180 | 64% |
| JN181 | 62% |
| JN182 | 58% |
| JN183 | 60% |
| JN184 | 55% |
| JN226 | 62% |

Example 12: *Aspergillus niger* Asparaginase Variants

*Aspergillus niger* asparaginase gene and its variant genes were introduced into *S. cerevisiae* as *Aspergillus oryzae* asaparaginase gene, and the residual activities were compared as described in Example 3.

TABLE 11

Residual activity after incubation at elevated temeparatures

| | Seq. number of the corresponding amino acid of *A. oryzae* asparaginase | | Residual activity after 20 min-incubation at | | |
|---|---|---|---|---|---|
| | | | 60° C. | 63° C. | 66° C. |
| *A. niger* asparaginase wild type | | | 63% | 19% | 2% |
| JN267 | K118A | K122 | 63% | 28% | 3% |
| JN269 | P237E | P241 | 73% | 52% | 3% |
| JN270 | Q286V | K290 | 81% | 50% | 3% |
| JN274 | S334W | S338 | 89% | 86% | 69% |

Example 13: Asparaginase Activity Assay—Used in Example 14

Principle

Asparaginase hydrolyses asparagine to aspartic acid and ammonium. Produced ammonium is determined using Nessler's reagent.

Activity is determined relative to a standard of known activity in ASNU or to a relevant control sample. Activity as determined according to this assay is referred to as nASNU.

Enzyme Incubation

| | |
|---|---|
| Temperature | 37° C. |
| pH | 6.0 |
| Buffer | 20 mM citric acid, pH 6 + 0.001% triton x-100 |
| Asparagine substrate sol. | 25 mg/ml in buffer |
| Stop reagent | 1.5M Trichloroacetic acid (TCA) |
| Enzyme Standard | 0-20 ASNU/ml |
| | The enzyme dilutions are made in buffer |
| Incubation time | 10 min |

Procedure:

| | |
|---|---|
| Buffer | 750 μL |
| Asparagine (25 mg/mL) | 100 μL |
| Sample | 100 μL |
| 1.5M TCA (stop reagent) | 50 μL |
| Total volume | 1,000 μL |

Mix buffer and asparagine and let it equilibrate at 37° C. for 10-15 min. Add enzyme standard or sample and incubate for 10 min at 37° C. Add TCA to stop the reaction.

Ammonium Determination (Nessler Assay)

| | |
|---|---|
| Temperature | Ambient |
| pH | ~12, controlled by addition of Nesslers reagent |
| Nessler's reagent | Mercury(II)chloride, potassium iodide, potassium hydroxide |
| Incubation time | 10 min |
| $A_{436}$ | Endpoint measurement at 440 nm |

Procedure:

| | Microtiter plate |
|---|---|
| Milli-Q Water | 140 μL |
| Sample | 20 μL |
| Nessler's reagent | 40 μL |
| Total volume | 200 μL |

Milli-Q water, sample and Nessler's reagent is added to the microtiter plate. Shake for 10 sec and then leave to incubate for 10 min before shaking again and reading at 440 nm.

Example 14: Testing the Effect of NaCl and Xylitol on Enzyme Activity

To test the effect of NaCl or xylitol on asparaginase activity, the compounds were added directly to the buffer and asparaginase activity measured using the standard assay described in Example 13. NaCl was tested in two concentrations and xylitol in one.

Buffers used were:
Buffer: 20 mM citric acid buffer, pH 6, 0.001% triton X100:
Xylitol: 70.8 g buffer+29.2 g xylitol
NaCl-1: 91.8 g buffer+8.2 g sodium chloride
NaCl-2: 84 g buffer+16 g sodium chloride The measured activity in the presence of either NaCl or xylitol was compared to the activity in buffer without NaCl and xylitol (set as 100%). Results are shown below.

| | % activity NaCl-1 | % activity xylitol | % activity NaCl2 |
|---|---|---|---|
| Wt enzyme | 41 | 158 | 26 |
| JN179 | 112 | 102 | 87 |
| JN181 | 107 | 82 | 88 |
| A. niger wt asparaginase | 141 | 176 | 129 |

As seen from the results the activity of the variants are less affected by NaCl and xylitol than the wt enzyme.

Example 15: Km and kcat Determination

Purified enzyme was diluted with 20 mM sodium acetate buffer pH 5.5 to a solution of a specified activity around 2 rASNU/ml. Ten microliters of enzyme solution was added to 100 microL of preincubated substrate solution containing L-asparagine in different concentration (0.22-26.6 mM) constructed by dissolving L-asparagine monohydrate in 100 mM sodium acetate buffer pH 5.0 including 0.02% TritonX-100. After 10 min incubation at 50° C., the amount of generated ammonia in the reaction mixture was measured by using Ammonia Test Kit (Wako Pure Chemicals, Japan) following the package insert protocol. The Km and Vmax were determined from Michaelis-Menten equation, and kcat was calculated using Vmax.

| | Km [mM] | kcat [sec$^{-1}$] |
|---|---|---|
| WT | 0.95 | 121.1 |
| JN161 | 0.69 | 171.5 |
| JN167 | 0.67 | 126.8 |
| JN178 | 0.88 | 127.1 |
| JN180 | 0.83 | 185.1 |
| JN181 | 0.58 | 138.3 |
| JN182 | 0.91 | 186.5 |
| JN183 | 0.91 | 188.6 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An asparaginase variant comprising
   (i) one or more of the following substitutions, wherein each position corresponds to a position in SEQ ID NO: 2: T71C, T74A, T74C, K122A, K122R, V139G, K194L, D197E, I228M, S238C, N239C, K240R, K253R, I258V, I258Y, R259C, R259V, S297V, S299A, T314A, P333L, S334P, S334W, E337S, S338G, S338W, G356D, K363R or E373H, or
   (ii) a deletion at one or more positions corresponding to positions 28 or 29 of SEQ ID NO: 2;
wherein the variant has at least 90% sequence identity to the mature polypeptide of any of SEQ ID NO: 2 or 4, and wherein the variant has asparaginase activity.

2. The asparaginase variant of claim 1, which comprises K122A.

3. The asparaginase variant of claim 1, which comprises S299A.

4. The asparaginase variant of claim 1, which comprises S334P.

5. The asparaginase variant of claim 1, which comprises E337S.

6. The variant of claim 1, which has at least 95% sequence identity to the mature polypeptide of any of SEQ ID NO: 2.

7. The variant of claim 1, which has at least 95% sequence identity to the mature polypeptide of any of SEQ ID NO: 4.

8. The variant of claim 1, which has an improved thermostability relative to the asparaginase encoded by SEQ ID NO: 2.

9. The variant of claim 1, which has an improved thermostability relative to the asparaginase encoded by SEQ ID NO: 6.

10. The variant of claim 1, which further comprises a substitution at one or more positions corresponding to positions 70, 290, 307, 323, 327, 349, 351 or 353 of SEQ ID NO: 2.

11. The variant of claim 10, wherein the substitution is N70K, K290V, S307A, A323R, T327V, A349Q, S351A or V353I.

12. The variant of claim 1, wherein the mature polypeptide is amino acids 27 to 378 of SEQ ID NO: 2.

13. A method for producing a food product from a food material, comprising:
   a. adding the variant of claim 1 to the food material; and
   b. heating the enzyme treated food material.

14. A method for producing a food product from a food material, comprising:
   a. adding the variant of claim 2 to the food material; and
   b. heating the enzyme treated food material.

15. A method for producing a food product from a food material, comprising:
   a. adding the variant of claim 3 to the food material; and
   b. heating the enzyme treated food material.

16. A method for producing a food product from a food material, comprising:
   a. adding the variant of claim 4 to the food material; and
   b. heating the enzyme treated food material.

17. A method for producing a food product from a food material, comprising:
   a. adding the variant of claim 5 to the food material; and
   b. heating the enzyme treated food material.

18. A method for producing a food product from a food material, comprising:
   a. adding the variant of claim 6 to the food material; and
   b. heating the enzyme treated food material.

19. A method for producing a food product from a food material, comprising:
   a. adding the variant of claim 7 to the food material; and
   b. heating the enzyme treated food material.

* * * * *

UNITED STATES PATENT AND TRADEMARK OFFICE
CERTIFICATE OF CORRECTION

| | |
|---|---|
| PATENT NO. | : 10,472,617 B2 |
| APPLICATION NO. | : 15/714292 |
| DATED | : November 12, 2019 |
| INVENTOR(S) | : Tomoko Matsui et al. |

Page 1 of 1

It is certified that error appears in the above-identified patent and that said Letters Patent is hereby corrected as shown below:

In the Claims

Column 104, In Claim 11, Line 2, please delete "5307A" and insert --S307A--.

Signed and Sealed this
Sixteenth Day of June, 2020

Andrei Iancu
*Director of the United States Patent and Trademark Office*

SEQUENCE LISTING

<160> NUMBER OF SEQ ID NOS: 10

<210> SEQ ID NO 1
<211> LENGTH: 1137
<212> TYPE: DNA
<213> ORGANISM: Aspergillus oryzae

<400> SEQUENCE: 1

| | | | | |
|---|---|---|---|---|
| atgggtgtca atttcaaagt tcttgccctg tcggccttag ctactattag ccatgcttcg | | | | | 60 |
| cctctcctat atcctcgagc cacagactcg aacgtcacct atgtgttcac caaccccaat | | | | | 120 |
| ggcctgaact ttactcagat gaacaccacc ctgccaaacg tcactatctt cgcgacaggc | | | | | 180 |
| ggcacaatcg cgggctccag cgccgacaac accgcaacaa caggttacaa agccggtgca | | | | | 240 |
| gtcggcatcc agacactgat cgacgcggtc ccggaaatgc taaacgttgc caacgtcgct | | | | | 300 |
| ggcgtgcaag taaccaatgt cggcagccca gacatcacct ccgacattct cctgcgtctc | | | | | 360 |
| tccaaacaga tcaacgaggt ggtctgcaac gaccccacca tggccggtgc agtggtcacc | | | | | 420 |
| cacggcaccg acacgctcga agaatccgcc ttcttcctcg acgccacggt caactgtcgc | | | | | 480 |
| aagcccgtgg tcatcgtcgg cgccatgcgc ccttcaaccg ccatctcggc tgacggcccc | | | | | 540 |
| ctcaacctcc tgcaatccgt caccgtcgcc gcgagcccca aggcccgaga ccgcggcgcc | | | | | 600 |
| ctgattgtca tgaacgaccg catcgtatcc gccttctacg cctccaagac gaacgccaac | | | | | 660 |
| accgtcgata cattcaaggc catcgaaatg ggtaacctgg gcgaggtcgt ctccaacaaa | | | | | 720 |
| ccctacttct tctaccccc agtcaagcca acaggcaaga cggaagtaga tatccggaac | | | | | 780 |
| atcacctcca tccccagagt cgacatcctc tactcatacg aagacatgca caatgacacc | | | | | 840 |
| ctttactccg ccatcgacaa cggcgcaaag ggcatcgtta tcgccggctc cggctccggc | | | | | 900 |
| tccgtctcca ccccccttcag cgccgccatg aagacatca aaccaaaca caacatcccc | | | | | 960 |
| atcgtagcca gcacgcgcac cggaaacggg gaggtgccgt cctccgccga gtcgagccag | | | | | 1020 |
| atcgcaagcg ggtatttgaa ccccgcaaag tcacgcgttt tgcttggctt gttgcttgcc | | | | | 1080 |
| caggggaaga gtattgagga aatgagggcg gtttttgagc ggattggggt tgcttga | | | | | 1137 |

<210> SEQ ID NO 2
<211> LENGTH: 378
<212> TYPE: PRT
<213> ORGANISM: Aspergillus oryzae

<400> SEQUENCE: 2

Met Gly Val Asn Phe Lys Val Leu Ala Leu Ser Ala Leu Ala Thr Ile
1               5                   10                  15

Ser His Ala Ser Pro Leu Leu Tyr Pro Arg Ala Thr Asp Ser Asn Val
            20                  25                  30

Thr Tyr Val Phe Thr Asn Pro Asn Gly Leu Asn Phe Thr Gln Met Asn
        35                  40                  45

Thr Thr Leu Pro Asn Val Thr Ile Phe Ala Thr Gly Gly Thr Ile Ala
    50                  55                  60

Gly Ser Ser Ala Asp Asn Thr Ala Thr Thr Gly Tyr Lys Ala Gly Ala
65                  70                  75                  80

Val Gly Ile Gln Thr Leu Ile Asp Ala Val Pro Glu Met Leu Asn Val
                85                  90                  95

Ala Asn Val Ala Gly Val Gln Val Thr Asn Val Gly Ser Pro Asp Ile
            100                 105                 110

Thr Ser Asp Ile Leu Leu Arg Leu Ser Lys Gln Ile Asn Glu Val Val
        115                 120                 125

| | | | | | | | | | | |
|---|---|---|---|---|---|---|---|---|---|---|
Cys | Asn | Asp | Pro | Thr | Met | Ala | Gly | Ala | Val | Val | Thr | His | Gly | Thr | Asp
 | 130 | | | | 135 | | | | 140 | |

Thr Leu Glu Glu Ser Ala Phe Phe Leu Asp Ala Thr Val Asn Cys Arg
145                 150                 155                 160

Lys Pro Val Val Ile Val Gly Ala Met Arg Pro Ser Thr Ala Ile Ser
                165                 170                 175

Ala Asp Gly Pro Leu Asn Leu Leu Gln Ser Val Thr Val Ala Ala Ser
            180                 185                 190

Pro Lys Ala Arg Asp Arg Gly Ala Leu Ile Val Met Asn Asp Arg Ile
        195                 200                 205

Val Ser Ala Phe Tyr Ala Ser Lys Thr Asn Ala Asn Thr Val Asp Thr
    210                 215                 220

Phe Lys Ala Ile Glu Met Gly Asn Leu Gly Glu Val Val Ser Asn Lys
225                 230                 235                 240

Pro Tyr Phe Phe Tyr Pro Val Lys Pro Thr Gly Lys Thr Glu Val
                245                 250                 255

Asp Ile Arg Asn Ile Thr Ser Ile Pro Arg Val Asp Ile Leu Tyr Ser
            260                 265                 270

Tyr Glu Asp Met His Asn Asp Thr Leu Tyr Ser Ala Ile Asp Asn Gly
        275                 280                 285

Ala Lys Gly Ile Val Ile Ala Gly Ser Gly Ser Gly Ser Val Ser Thr
    290                 295                 300

Pro Phe Ser Ala Ala Met Glu Asp Ile Thr Thr Lys His Asn Ile Pro
305                 310                 315                 320

Ile Val Ala Ser Thr Arg Thr Gly Asn Gly Glu Val Pro Ser Ser Ala
                325                 330                 335

Glu Ser Ser Gln Ile Ala Ser Gly Tyr Leu Asn Pro Ala Lys Ser Arg
            340                 345                 350

Val Leu Leu Gly Leu Leu Leu Ala Gln Gly Lys Ser Ile Glu Glu Met
        355                 360                 365

Arg Ala Val Phe Glu Arg Ile Gly Val Ala
    370                 375

<210> SEQ ID NO 3
<211> LENGTH: 1137
<212> TYPE: DNA
<213> ORGANISM: Artificial Sequence
<220> FEATURE:
<223> OTHER INFORMATION: Variant

<400> SEQUENCE: 3

```
atgggtgtca atttcaaagt tcttgccctg tcggccttag ctactattag ccatgcttcg      60
cctctcctat atcctcgagc cacagactcg aacgtcacct atgtgttcac caaccccaat     120
ggcctgaact ttactcagat gaacaccacc ctgccaaacg tcactatctt cgcgacaggc     180
ggcacaatcg cgggctccag cgccgacaag accgcaacaa caggttacaa agccggtgca     240
gtcggcatcc agacactgat cgacgcggtc ccggaaatgc taaacgttgc caacgtcgct     300
ggcgtgcaag taaccaatgt cggcagccca gacatcacct ccgacattct cctgcgtctc     360
tccaaacaga tcaacgaggt ggtctgcaac gaccccacca tggccggtgc agtggtcacc     420
cacggcaccg acacgctcga agaatccgcc ttcttcctcg acgccacggt caactgtcgc     480
aagcccgtgg tcatcgtcgg cgccatgcgc ccttcaaccg ccatctcggc tgacggcccc     540
ctcaacctcc tgcaatccgt caccgtcgcc gcgagcccca aggcccgaga ccgcggcgcc     600
```

```
ctgattgtca tgaacgaccg catcgtatcc gccttctacg cctccaagac gaacgccaac    660
accgtcgata cattcaaggc catcgaaatg ggtaacctgg gcgaggtcgt ctccaacaaa    720
ccctacttct tctaccccc agtcaagcca acaggcaaga cggaagtaga tatccggaac    780
atcacctcca tccccagagt cgacatcctc tactcatacg aagacatgca caatgacacc    840
ctttactccg ccatcgacaa cggcgcaaag ggcatcgtta tcgccggctc cggctccggc    900
tccgtctcca cccccttcgc ggccgccatg aagacatca caaccaaaca caacatcccc    960
atcgtacgca gcacccgcgt cggaaacggg gaggtgccgt cctccgccga gtcgagccag   1020
atcgcaagcg ggtatttgaa cccccagaag gcccgcatct tgcttggctt gttgcttgcc   1080
caggggaaga gtattgagga aatgagggcg ttttttgagc ggattggggt tgcttga      1137
```

<210> SEQ ID NO 4
<211> LENGTH: 378
<212> TYPE: PRT
<213> ORGANISM: Artificial Sequence
<220> FEATURE:
<223> OTHER INFORMATION: Variant

<400> SEQUENCE: 4

```
Met Gly Val Asn Phe Lys Val Leu Ala Leu Ser Ala Leu Ala Thr Ile
1               5                   10                  15

Ser His Ala Ser Pro Leu Leu Tyr Pro Arg Ala Thr Asp Ser Asn Val
            20                  25                  30

Thr Tyr Val Phe Thr Asn Pro Asn Gly Leu Asn Phe Thr Gln Met Asn
        35                  40                  45

Thr Thr Leu Pro Asn Val Thr Ile Phe Ala Thr Gly Gly Thr Ile Ala
    50                  55                  60

Gly Ser Ser Ala Asp Lys Thr Ala Thr Thr Gly Tyr Lys Ala Gly Ala
65                  70                  75                  80

Val Gly Ile Gln Thr Leu Ile Asp Ala Val Pro Glu Met Leu Asn Val
                85                  90                  95

Ala Asn Val Ala Gly Val Gln Val Thr Asn Val Gly Ser Pro Asp Ile
            100                 105                 110

Thr Ser Asp Ile Leu Leu Arg Leu Ser Lys Gln Ile Asn Glu Val Val
        115                 120                 125

Cys Asn Asp Pro Thr Met Ala Gly Ala Val Val Thr His Gly Thr Asp
    130                 135                 140

Thr Leu Glu Glu Ser Ala Phe Phe Leu Asp Ala Thr Val Asn Cys Arg
145                 150                 155                 160

Lys Pro Val Val Ile Val Gly Ala Met Arg Pro Ser Thr Ala Ile Ser
                165                 170                 175

Ala Asp Gly Pro Leu Asn Leu Leu Gln Ser Val Thr Val Ala Ala Ser
            180                 185                 190

Pro Lys Ala Arg Asp Arg Gly Ala Leu Ile Val Met Asn Asp Arg Ile
        195                 200                 205

Val Ser Ala Phe Tyr Ala Ser Lys Thr Asn Ala Asn Thr Val Asp Thr
    210                 215                 220

Phe Lys Ala Ile Glu Met Gly Asn Leu Gly Glu Val Val Ser Asn Lys
225                 230                 235                 240

Pro Tyr Phe Phe Tyr Pro Pro Val Lys Pro Thr Gly Lys Thr Glu Val
                245                 250                 255

Asp Ile Arg Asn Ile Thr Ser Ile Pro Arg Val Asp Ile Leu Tyr Ser
            260                 265                 270
```

Tyr Glu Asp Met His Asn Asp Thr Leu Tyr Ser Ala Ile Asp Asn Gly
            275                 280                 285

Ala Lys Gly Ile Val Ile Ala Gly Ser Gly Ser Gly Ser Val Ser Thr
        290                 295                 300

Pro Phe Ala Ala Ala Met Glu Asp Ile Thr Thr Lys His Asn Ile Pro
305                 310                 315                 320

Ile Val Arg Ser Thr Arg Val Gly Asn Gly Glu Val Pro Ser Ser Ala
                325                 330                 335

Glu Ser Ser Gln Ile Ala Ser Gly Tyr Leu Asn Pro Gln Lys Ala Arg
            340                 345                 350

Ile Leu Leu Gly Leu Leu Leu Ala Gln Gly Lys Ser Ile Glu Glu Met
        355                 360                 365

Arg Ala Val Phe Glu Arg Ile Gly Val Ala
    370                 375

<210> SEQ ID NO 5
<211> LENGTH: 1137
<212> TYPE: DNA
<213> ORGANISM: Artificial Sequence
<220> FEATURE:
<223> OTHER INFORMATION: Variant

<400> SEQUENCE: 5
atgggtgtca atttcaaagt tcttgccctg tcggccttag ctactattag ccatgcttcg      60
cctctcctat atcctcgagc cacagactcg aacgtcacct atgtgttcac caaccccaat    120
ggcctgaact ttactcagat gaacaccacc ctgccaaacg tcactatctt cgcgacaggc    180
ggcacaatcg cgggctccag cgccgacaag accgcaacaa caggttacaa agccggtgca    240
gtcggcatcc agacactgat cgacgcggtc ccggaaatgc taaacgttgc caacgtcgct    300
ggcgtgcaag taaccaatgt cggcagccca gacatcacct ccgacattct cctgcgtctc    360
tccaaacaga tcaacgaggt ggtctgcaac gaccccacca tggccggtgc agtggtcacc    420
cacggcaccg acacgctcga agaatccgcc ttcttcctcg acgccacggt caactgtcgc    480
aagcccgtgg tcatcgtcgg cgccatgcgc ccttcaaccg ccatctcggc tgacggcccc    540
ctcaacctcc tgcaatccgt caccgtcgcc gcgagcccca aggcccgaga ccgcggcgcc    600
ctgattgtca tgaacgaccg catcgtatcc gccttctacg cctccaagac gaacgccaac    660
accgtcgata cattcaaggc catcgaaatg gtaacctggg cgaggtcgt ctccaacaaa     720
ccctacttct tctaccccccc agtcaagcca acaggcaaga cggaagtaga tatccggaac    780
atcacctcca tccccagagt cgacatcctc tactcatacg aagacatgca caatgacacc    840
ctttactccg ccatcgacaa cggcgcaaag ggcatcgtta tcgccggctc cggctccggc    900
tccgtctcca cccccttcag cgccgccatg aagacatca caaccaaaca caacatcccc    960
atcgtacgca gcacccgcgt cggaaacggg gaggtgccgt cctccgccga gtcgagccag   1020
atcgcaagcg ggtatttgaa cccccagaag gcccgcatct gcttggctt gttgcttgcc   1080
caggggaaga gtattgagga aatgagggcg gtttttgagc ggattggggt tgcttga      1137

<210> SEQ ID NO 6
<211> LENGTH: 378
<212> TYPE: PRT
<213> ORGANISM: Artificial Sequence
<220> FEATURE:
<223> OTHER INFORMATION: Variant

<400> SEQUENCE: 6

```
Met Gly Val Asn Phe Lys Val Leu Ala Leu Ser Ala Leu Ala Thr Ile
 1               5                  10                  15

Ser His Ala Ser Pro Leu Leu Tyr Pro Arg Ala Thr Asp Ser Asn Val
            20                  25                  30

Thr Tyr Val Phe Thr Asn Pro Asn Gly Leu Asn Phe Thr Gln Met Asn
        35                  40                  45

Thr Thr Leu Pro Asn Val Thr Ile Phe Ala Thr Gly Gly Thr Ile Ala
 50                  55                  60

Gly Ser Ser Ala Asp Lys Thr Ala Thr Thr Gly Tyr Lys Ala Gly Ala
 65                  70                  75                  80

Val Gly Ile Gln Thr Leu Ile Asp Ala Val Pro Glu Met Leu Asn Val
                85                  90                  95

Ala Asn Val Ala Gly Val Gln Val Thr Asn Val Gly Ser Pro Asp Ile
                100                 105                 110

Thr Ser Asp Ile Leu Leu Arg Leu Ser Lys Gln Ile Asn Glu Val Val
            115                 120                 125

Cys Asn Asp Pro Thr Met Ala Gly Ala Val Val Thr His Gly Thr Asp
130                 135                 140

Thr Leu Glu Glu Ser Ala Phe Phe Leu Asp Ala Thr Val Asn Cys Arg
145                 150                 155                 160

Lys Pro Val Val Ile Val Gly Ala Met Arg Pro Ser Thr Ala Ile Ser
                165                 170                 175

Ala Asp Gly Pro Leu Asn Leu Leu Gln Ser Val Thr Val Ala Ala Ser
            180                 185                 190

Pro Lys Ala Arg Asp Arg Gly Ala Leu Ile Val Met Asn Asp Arg Ile
        195                 200                 205

Val Ser Ala Phe Tyr Ala Ser Lys Thr Asn Ala Asn Thr Val Asp Thr
210                 215                 220

Phe Lys Ala Ile Glu Met Gly Asn Leu Gly Glu Val Val Ser Asn Lys
225                 230                 235                 240

Pro Tyr Phe Phe Tyr Pro Pro Val Lys Pro Thr Gly Lys Thr Glu Val
                245                 250                 255

Asp Ile Arg Asn Ile Thr Ser Ile Pro Arg Val Asp Ile Leu Tyr Ser
            260                 265                 270

Tyr Glu Asp Met His Asn Asp Thr Leu Tyr Ser Ala Ile Asp Asn Gly
        275                 280                 285

Ala Lys Gly Ile Val Ile Ala Gly Ser Gly Ser Gly Ser Val Ser Thr
290                 295                 300

Pro Phe Ser Ala Ala Met Glu Asp Ile Thr Thr Lys His Asn Ile Pro
305                 310                 315                 320

Ile Val Arg Ser Thr Arg Val Gly Asn Gly Glu Val Pro Ser Ser Ala
                325                 330                 335

Glu Ser Ser Gln Ile Ala Ser Gly Tyr Leu Asn Pro Gln Lys Ala Arg
            340                 345                 350

Ile Leu Leu Gly Leu Leu Leu Ala Gln Gly Lys Ser Ile Glu Glu Met
        355                 360                 365

Arg Ala Val Phe Glu Arg Ile Gly Val Ala
    370                 375

<210> SEQ ID NO 7
<211> LENGTH: 20
<212> TYPE: DNA
<213> ORGANISM: Artificial Sequence
<220> FEATURE:
<223> OTHER INFORMATION: Primer
```

<400> SEQUENCE: 7
taggagttta gtgaacttgc                                                    20

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ttcgagcgtc ccaaaacc                                                      18

<210> SEQ ID NO 9
<211> LENGTH: 18
<212> TYPE: PRT
<213> ORGANISM: Humicola insolens

<400> SEQUENCE: 9

Met Lys Phe Phe Thr Thr Ile Leu Ser Thr Ala Ser Leu Val Ala Ala
1               5                   10                  15

Leu Pro

<210> SEQ ID NO 10
<211> LENGTH: 378
<212> TYPE: PRT
<213> ORGANISM: Aspergillus niger

<400> SEQUENCE: 10

Met Pro Leu Lys Pro Ile Leu Leu Ser Ala Leu Ala Ser Leu Ala Ser
1               5                   10                  15

Ala Ser Pro Leu Leu Tyr Ser Arg Thr Thr Asn Glu Thr Phe Val Phe
                20                  25                  30

Thr Asn Ala Asn Gly Leu Asn Phe Thr Gln Met Asn Thr Thr Leu Pro
        35                  40                  45

Asn Val Thr Ile Phe Ala Thr Gly Gly Thr Ile Ala Gly Ser Asp Ser
    50                  55                  60

Ser Ser Thr Ala Thr Thr Gly Tyr Thr Ser Gly Ala Val Gly Val Leu
65                  70                  75                  80

Ser Leu Ile Asp Ala Val Pro Ser Met Leu Asp Val Ala Asn Val Ala
                85                  90                  95

Gly Val Gln Val Ala Asn Val Gly Ser Glu Asp Ile Thr Ser Asp Ile
                100                 105                 110

Leu Ile Ser Met Ser Lys Lys Leu Asn Arg Val Val Cys Glu Asp Pro
            115                 120                 125

Thr Met Ala Gly Ala Val Ile Thr His Gly Thr Asp Thr Leu Glu Glu
        130                 135                 140

Thr Ala Phe Phe Leu Asp Ala Thr Val Asn Cys Gly Lys Pro Ile Val
145                 150                 155                 160

Ile Val Gly Ala Met Arg Pro Ser Thr Ala Ile Ser Ala Asp Gly Pro
                165                 170                 175

Phe Asn Leu Leu Glu Ala Val Thr Val Ala Ala Ser Thr Ser Ala Arg
            180                 185                 190

Asp Arg Gly Ala Met Val Val Met Asn Asp Arg Ile Ala Ser Ala Tyr
        195                 200                 205

Tyr Val Thr Lys Thr Asn Ala Asn Thr Met Asp Thr Phe Lys Ala Met
    210                 215                 220

-continued

```
Glu Met Gly Tyr Leu Gly Glu Met Ile Ser Asn Thr Pro Phe Phe Phe
225             230             235             240

Tyr Pro Pro Val Lys Pro Thr Gly Lys Val Ala Phe Asp Ile Thr Asn
            245             250             255

Val Thr Glu Ile Pro Arg Val Asp Ile Leu Phe Ser Tyr Glu Asp Met
            260             265             270

His Asn Asp Thr Leu Tyr Asn Ala Ile Ser Ser Gly Ala Gln Gly Ile
            275             280             285

Val Ile Ala Gly Ala Gly Ala Gly Gly Val Thr Thr Ser Phe Asn Glu
    290             295             300

Ala Ile Glu Asp Val Ile Asn Arg Leu Glu Ile Pro Val Val Gln Ser
305             310             315             320

Met Arg Thr Val Asn Gly Glu Val Pro Leu Ser Asp Val Ser Ser Asp
            325             330             335

Thr Ala Thr His Ile Ala Ser Gly Tyr Leu Asn Pro Gln Lys Ser Arg
            340             345             350

Ile Leu Leu Gly Leu Leu Leu Ser Gln Gly Lys Asn Ile Thr Glu Ile
            355             360             365

Ala Asp Val Phe Ala Leu Gly Thr Asp Ala
370             375
```